United States Patent
Wu et al.

[11] Patent Number: 5,965,491
[45] Date of Patent: Oct. 12, 1999

[54] PESTICIDAL 1-ARYL-3-IMINOPYRAZOLES

[75] Inventors: Tai-Teh Wu, Chapel Hill; David Treadway Manning, Cary, both of N.C.

[73] Assignee: Rhone-Poulenc Inc., Research Triangle Park, N.C.

[21] Appl. No.: 09/036,794

[22] Filed: Mar. 9, 1998

Related U.S. Application Data

[60] Provisional application No. 60/040,135, Mar. 10, 1997.

[51] Int. Cl.$^6$ .................. C07D 215/38; C07D 401/00; C07D 277/82; C07D 239/02
[52] U.S. Cl. .................. 504/253; 504/280; 514/256; 514/313; 514/341; 514/367; 514/370; 514/406; 546/159; 546/275.4; 548/364.4; 548/365.1; 548/364.1; 548/190; 548/161; 544/333; 544/335
[58] Field of Search .................. 514/341, 406, 514/256, 313, 370, 367; 546/275.4, 159; 548/364.4, 365.1, 364.1, 190, 161; 544/333, 335; 504/253, 280

[56] References Cited

U.S. PATENT DOCUMENTS

| | | | |
|---|---|---|---|
| 4,614,533 | 9/1986 | Schallner et al. | 504/282 |
| 4,804,675 | 2/1989 | Jensen-Korte et al. | 514/407 |
| 4,810,720 | 3/1989 | Jensen-Korte et al. | 514/407 |
| 4,954,165 | 9/1990 | Jensen-Korte et al. | 548/367.4 |
| 5,047,550 | 9/1991 | D'Silva | 548/366.7 |
| 5,079,370 | 1/1992 | D'Silva et al. | 548/366.7 |
| 5,104,439 | 4/1992 | Schallner et al. | 504/282 |
| 5,104,994 | 4/1992 | Roberts et al. | 548/366.7 |
| 5,187,185 | 2/1993 | Outcalt et al. | 514/408 |
| 5,223,525 | 6/1993 | Wu et al. | 514/398 |
| 5,232,940 | 8/1993 | Hatton et al. | 514/407 |
| 5,256,634 | 10/1993 | Schallnor et al. | 548/282 |
| 5,306,694 | 4/1994 | Phillips et al. | 504/253 |

FOREIGN PATENT DOCUMENTS

| | | |
|---|---|---|
| 0 154 115 | 1/1985 | European Pat. Off. . |
| 0 201 852 | 11/1986 | European Pat. Off. . |
| 0 295 117 | 12/1988 | European Pat. Off. . |
| 0 352 944 | 1/1990 | European Pat. Off. . |
| 0 403 309 | 12/1990 | European Pat. Off. . |
| 0 418 016 | 3/1991 | European Pat. Off. . |
| WO 87/03781 | 7/1987 | WIPO . |
| WO 93/06089 | 4/1993 | WIPO . |
| WO94/21606 | 9/1994 | WIPO . |
| WO 97/28126 | 8/1997 | WIPO . |

*Primary Examiner*—D Margaret M. Mach
*Attorney, Agent, or Firm*—Finnegan, Henderson, Farabow, Garrett & Dunner, L.L.P.

[57] ABSTRACT

1-Aryl-3-iminopyrazoles of the formula:

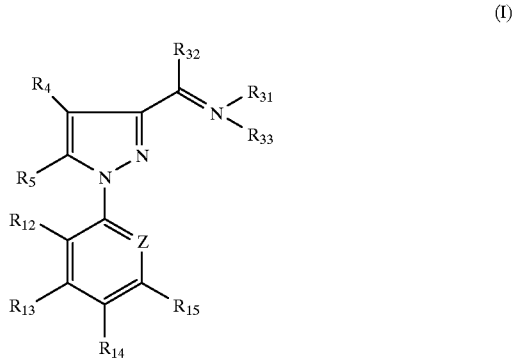

(I)

wherein $R_{31}$, $R_{32}$, $R_{33}$, $R_4$, $R_5$, $R_{12}$, $R_{13}$, $R_{14}$, $R_{15}$ and Z are as defined in the specification, are useful as pesticides or as intermediates to other pesticides. Compositions comprising the compounds of formula (I) and methods for their use, particularly in agriculture or for animal protection, as pesticides, especially for controlling arthropods, are described.

44 Claims, No Drawings

PESTICIDAL 1-ARYL-3-IMINOPYRAZOLES

CROSS-REFERENCE TO RELATED APPLICATION

This application claims the priority of copending U.S. Provisional Patent Application No. 60/040,135, filed Mar. 10, 1997, incorporated by reference herein in its entirety and relied upon.

BACKGROUND OF THE INVENTION

1. Field of the Invention

The invention relates to new derivatives of 1-arylpyrazoles which have some valuable properties either as pesticides or as intermediates to make other pesticides. The invention further pertains to compositions of said compounds and methods, using said compounds either as intermediates to make other pesticides, or for the control of arthropod pests, in particular to the application of said compounds or compositions in agricultural methods of use or for animal protection, particularly as pesticides, for controlling arthropods.

2. Description of the Related Art

International Patent Publication No. WO 87/03781 and European Patent Publications No. 0295117, 0154115 and 0201852 describe insecticidal 1-(substituted phenyl) pyrazoles. Other prior art is also found in the text of these patent applications or the patents issued therefrom.

International Patent Publications No. WO 93/06089 and WO 94/21606 also describe insecticidal 1-(4-SF$_5$ substituted phenyl)heterocycles which may be pyrroles as well as imidazoles or pyrazoles. The teaching of these patents is not substantially different from International Patent Publication No. WO 87/03781 or from European Patent Publication No. 0295117 as far as pyrazoles are concerned.

Various pesticidal pyrazoles have been disclosed in various patents or patent applications: European 0418016, 0403309, 0352944; U.S. Pat. Nos. 5,104,994, 5,079,370, 5,047,550, 5,232,940, 4,810,720, 4,804,675, 5,306,694, 4,614,533, 5,187,185, 5,223,525; WO 93/06089, 94/21606 and WO 97/28126.

Due to the many existing pests and crops and conditions of attacks of crops by pests, there is a need for further novel pesticidal compounds.

OBJECTS AND SUMMARY OF THE INVENTION

It is an object of the present invention to provide new pesticidal compounds of the 1-arylpyrazole family together with processes for their preparation.

A second object of the present invention is to provide pesticidal compositions and pesticidal methods of use of the pesticidal pyrazole compounds against arthropods, especially insects, particularly in agricultural or horticultural crops, forestry, veterinary medicine or livestock husbandry, or in public health.

A third object of the present invention is to provide very active compounds, with broad spectrum pesticidal activity, as well as compounds with selective special activity, e.g., aphicidal, miticidal, foliar insecticidal, soil insecticidal, systemic, antifeeding or pesticidal activity via seed treatment.

These and other objects, which are met in whole or in part by the instant invention, shall become readily apparent from the description of the invention which follows.

This invention embraces novel chemical compounds having an insecticidal or miticidal or nematocidal or anthelminthic activity.

The invention thus relates to compounds having the general formula (I):

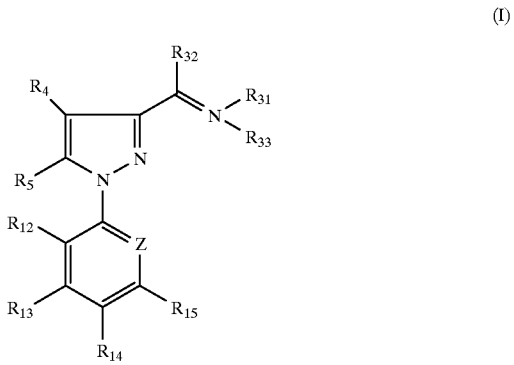

wherein:

$R_{31}$ may be:
- H; CN; NO$_2$; NO; SH; C$_1$–C$_6$ alkylthio; NH$_2$; P(O)(OR$_8$)(OR$_9$) or R$_{38}$; or
- mono(C$_1$–C$_6$ alkyl)amino; di(C$_1$–C$_6$ alkyl)amino; formyl(C$_1$–C$_6$ alkyl); C$_1$–C$_{20}$ alkyl; C$_3$–C$_6$ cycloalkyl; or C$_4$–C$_8$ (cycloalkyl)alkyl; each of which alkyl is optionally substituted by one or more R$_{35}$; or
- naphthyl or phenyl, each of which is optionally substituted by one or more R$_{36}$ or R$_{37}$; or
- NH—CO—NH—N=CR$_8$R$_9$; NH—CS—NH—N=CR$_8$R$_9$; NH—CO—NR$_8$R$_9$; NH—CS—NR$_8$R$_9$; NH—CO—OR$_8$; NH—CS—OR$_8$; or NH—CO—NH—NH$_2$;

$R_{32}$ may be alkyl (C$_1$–C$_6$), cycloalkyl (C$_3$–C$_7$), cycloalkylalkyl (C$_4$–C$_8$), each of which alkyl may be substituted by one or more R$_{35}$; phenyl optionally substituted by one or more R$_{36}$ or R$_{37}$; or R$_{38}$;

$R_{33}$ is a lone pair of electrons or an oxygen or sulfur atom (when R$_{33}$ is an oxygen or sulfur atom, it may be linked to the nitrogen atom by a covalent bond or a bond which may be partially covalent and partially ionic) or an alkyl (C$_1$–C$_6$) group, the nitrogen atom to which R$_{33}$ is linked being then in a cationic form N$^+$ (when R$_{33}$ is thus an alkyl group, the bond between the nitrogen atom and R$_{33}$ is a simple bond; and the compound of formula (I) is then an iminium salt); or R$_{31}$ and R$_{33}$ together form C$_2$–C$_6$ alkylene, wherein one or two of the carbon atoms is each optionally replaced by a heteroatom selected from the group consisting of O, S and N (the specificity of N and the bond between N and R$_{33}$ then being the same as indicated when R$_{33}$ is alkyl);

$R_{35}$ may be halogen, amino, C$_1$–C$_6$ alkylamino, di(C$_1$–C$_6$ alkyl)amino, NO$_2$, CN, C$_1$–C$_6$ alkoxy, (C$_1$–C$_6$ alkoxy)carbonyl, hydroxycarbonyl, (C$_1$–C$_6$ alkyl)carbonyl, methylene, methylidyne, acetenyl, acetenyl(C$_1$–C$_6$ alkyl); or R$_{35}$ may be phenyl optionally substituted by one or more R$_{36}$; or R$_{35}$ may be a heterocyclic ring having a total of 3 to 7 ring atoms of which 1 to 4 are heteroatoms, said heteroatoms being the same or different and being selected from the group consisting of O, S and N, said heterocyclic ring being saturated or unsaturated and being optionally substituted by one or more $R_{36}$; or $R_{35}$ may be OH, SH, $C_1$–$C_6$ alkylthio, $C_1$–$C_6$ alkylsulfinyl, $C_1$–$C_6$ alkylsulfonyl, aminocarbonyl, ($C_1$–$C_6$ alkyl)aminocarbonyl, di($C_1$–$C_6$ alkyl)aminocarbonyl, ($C_1$–$C_6$ alkoxy) carbonyl, or $P(O)(OR_8)(OR_9)$;

$R_{36}$ may be $SF_5$, halogen, $C_1$–$C_6$ alkyl, $C_1$–$C_6$ hydroxyalkyl, $NO_2$, CN, amino, $C_1$–$C_6$ alkylamino, di($C_1$–$C_6$ alkyl)amino, di($C_1$–$C_6$ alkyl) aminocarbonylamino, ($C_1$–$C_6$ alkyl) aminocarbonylamino, aminocarbonylamino, ($C_1$–$C_6$ alkyl)carbonyl, ($C_1$–$C_6$ alkoxy)carbonyl, ($C_1$–$C_6$ alkyl) carbonylamino, ($C_1$–$C_6$ alkoxy)carbonylamino, aminocarbonyl, di($C_1$–$C_6$ alkyl)aminocarbonyl, ($C_1$–$C_6$ alkyl)aminocarbonyl, hydroxycarbonyl, aminocarbonyloxy, ($C_1$–$C_6$ alkyl)aminocarbonyloxy, di($C_1$–$C_6$ alkyl)aminocarbonyloxy, hydroxy, $C_1$–$C_6$ alkoxy, $C_1$–$C_6$ haloalkyl, $C_1$–$C_6$ haloalkoxy, $C_1$–$C_6$ alkylthio, $C_1$–$C_6$ alkylsulfinyl, $C_1$–$C_6$ alkylsulfonyl, $C_1$–$C_6$ haloalkylthio, $C_1$–$C_6$ haloalkylsulfinyl, $C_1$–$C_6$ haloalkylsulfonyl, $P(O)(OR_8)(OR_9)$, ($C_1$–$C_6$ alkyl) [($C_1$–$C_6$ alkyl)carbonyl]amino or phenylamino($C_1$–$C_6$ alkyl);

$R_{37}$ may be $R_{36}$ or phenyl optionally substituted by one or more $R_{36}$, phenoxy optionally substituted by one or more $R_{36}$, or benzyl optionally substituted by one or more $R_{36}$;

$R_{38}$ may be a heterocyclic radical derived from a single heterocyclic ring or from a two ring fused heterocyclic system at least one ring of which is heterocyclic, each ring having 3 to 7 ring atoms, each heterocyclic ring having 1 to 4 hetero ring atoms, said hetero ring atoms being the same or different and being selected from the group consisting of O, S and N, each ring being saturated or unsaturated; such heterocyclic radicals may be, for example, radicals deriving from the following compounds: pyridine, pyrimidine, oxazole, oxadiazole, oxatriazole, isoxazole, thiazole, isothiazole, imidazole, pyrane, pyrone, pyrazole, pyrrole, tetrazole, furoxan, tetrahydrofuranyl, furan, pyrazine, pyridazine, benzimidazole, quinoline, isoquinoline, triazine, thiophene, furopyran, furopyrone, thiatriazine, thiadiazole, all of which heterocyclic radicals can be attached to the nitrogen of the $R_{32}$—C=N—$R_{31}$ group at any possible position of the heterocyclic ring and all of which rings may be optionally substituted with one or more $R_{36}$ or phenyl optionally substituted with one or more $R_{36}$;

$R_8$ and $R_9$ are independently selected from H and $C_1$–$C_6$ alkyl optionally having one or more substituents selected from the group consisting of halogen, $NO_2$, CN, CHO, OH, $C_1$–$C_6$ alkoxy, $C_1$–$C_6$ alkylthio, $C_1$–$C_6$ alkylsulfinyl, $C_1$–$C_6$ alkylsulfonyl, ($C_1$–$C_6$ alkoxy) carbonyl, hydroxycarbonyl, and carbamoyl;

$R_4$ is $R_{11}$ or $S(O)_n R_{11}$;

$R_{11}$ is $C_1$–$C_6$ alkyl, $C_3$–$C_6$ cycloalkyl, or $C_4$–$C_8$ (cycloalkyl)alkyl, each of which is optionally substituted by one or more halogen;

n is 0, 1 or 2;

$R_5$ is H, halogen, CN, $S(O)_n R_8$, $OR_8$, $NR_8R_9$, $N(R_8)CON(R_9)(R_8)$, azido, or —N=C($R_{10}$)($OR_9$);

$R_{10}$ may have the same meaning as $R_8$ and may be also benzyl or phenyl, optionally substituted by one or more $R_{36}$;

Z is N or C—$R_{16}$; and $R_{12}$ to $R_{16}$ may each be H, halogen, $R_8$, $OR_8$, $SF_5$, $S(O)_n R_8$, CN, $NO_2$, CHO, $C(O)R_8$, or $COOR_8$;

and pesticidally acceptable salts thereof.

DETAILED DESCRIPTION OF THE INVENTION AND PREFERRED EMBODIMENTS

All stereoisomers, geometric isomers (E & Z forms for imines), optical isomers and diastereomers having the general formula (I), as well as their tautomers if any, are included in the invention.

The salts of the hereinabove defined compounds are also included in the invention, especially the sodium, potassium or ammonium or iminium salts. Alkaline or alkaline earth or ammonium salts are generally derived from compounds of formula (I) wherein $R_{33}$ is an electron pair and $R_{31}$ is hydrogen. Iminium salts are generally derived from compounds of formula (I) wherein $R_{33}$ is an electron pair and $R_{31}$ is as defined above with formula (I).

Except where otherwise specified, the alkyl radicals and alkyl portions of other radicals herein contain from 1 to 20, preferably 1 to 10, more preferably 1 to 6 carbon atoms and can be straight- or branched-chain. Similarly, unless otherwise specified, the alkoxy radicals and alkoxy portions of other radicals contain 1 to 6 carbon atoms and can be straight- or branched-chain.

The alkyl portions of dialkylamino radicals and of other radicals which have dialkylamino portions can be the same or different, for example, N,N-dimethylamino, N,N-diethylamino and (N-ethyl-N-methyl)amino.

The word 'halo' used herein before the name of a radical means that the radical is substituted by one or more halogen atoms, which can be the same or different. Thus, the term 'haloalkyl' used herein means alkyl bearing as substituents one or more halogen atoms, which can be the same or different, and thus includes monohaloalkyl and polyhaloalkyl (that is, having more than one halogen substituent), the latter term in turn including perhaloalkyl (that is, being fully substituted by halogen atoms). The term 'haloalkoxy' similarly includes monohaloalkoxy and polyhaloalkoxy, the latter in turn including perhaloalkoxy.

The words 'halo' and 'halogen' mean F, Cl, Br or I. When more than one halogen atom is present as a substituent, such as on a phenyl ring, then they can be the same or different.

The invention further pertains to compositions of said compounds and methods, using said compounds, for the control of arthropod, nematode, helminth or protozoan pests. In particular, it pertains to the application of compounds or compositions thereof in agricultural methods of use, particularly as pesticides.

In the instant specification, the word imines is used to name compounds comprising the group C=NR.

In one aspect, the present invention provides compounds for use in controlling arthropod, nematode, helminth and protozoan pests, said compounds having the general formula (I). In another aspect, the present invention provides a pesticidal composition (i.e. an arthropodicidal, nematocidal, anti-helminth or anti-protozoal composition) comprising a pesticidally effective amount (i.e. an arthropodicidally effective amount, a nematocidally effective amount, an effective anti-helminth amount or an effective anti-protozoal amount) of a compound of formula (I) and an agriculturally acceptable inert carrier therefor. The expression 'a compound of formula (I)' used here and throughout this application includes within its ambit the various stereoisomeric forms of the compounds of formulas (I).

In yet another aspect, the invention provides a method for controlling arthropod, nematode, helminths or protozoan pests at a locus, said method comprising applying to said locus a pesticidally effective amount (i.e. an arthropodicidally or nematocidally effective amount or an effective antihelminth or anti-protozoal amount) of a compound of formula (I) or of a pesticidal composition as defined above.

Preferred compounds of the present invention have one or more of the following features:

$Z$ is $C—R_{16}$;

$R_{12}$ is chlorine or bromine;

$R_{13}$ and $R_{15}$ are H;

$R_{14}$ is perhaloalkyl, perhaloalkoxy or $SF_5$, preferably $CF_3$, $OCF_3$ or $SF_5$;

$R_{16}$ is chlorine or bromine;

$R_{31}$ is amino; alkyl optionally substituted by one or more $R_{35}$; phenyl optionally substituted by $R_{36}$ or $R_{37}$; $R_{38}$; NH—CO—NH—N=$CR_8R_9$; NH—CS—NH—N=$CR_8R_9$; NH—CO—$NR_8R_9$; NH—CS—$NR_8R_9$; NH—CO—$OR_8$; or NH—CS—$OR_8$;

$R_{32}$ is $C_1$ to $C_6$ alkyl, preferably methyl;

$R_{33}$ is a lone pair of electrons or oxygen, preferably a lone pair of electrons;

$R_4$ is $S(O)_nR_{11}$;

$R_{11}$ is methyl or ethyl;

n is 0 or 1, preferably 1;

$R_5$ is $NR_8R_9$; preferably $NH_2$ or $NHR_9$.

Preferred compounds of the present invention include one or more of the features set forth in connection with the following classes of preferred compounds:

A first class of preferred compounds comprises those wherein:
$R_{32}$ is $C_1$–$C_6$ alkyl; Z is C—$R_{16}$; $R_4$ is $S(O)_nR_{11}$; $R_{13}$ and $R_{15}$ are H; and $R_{14}$ is perhaloalkyl, perhaloalkoxy, or $SF_5$.

A second class of preferred compounds comprises those wherein:
$R_{32}$ is $CH_3$; $R_4$ is $S(O)_nR_{11}$; and $R_{11}$ is methyl or ethyl.

A third class of preferred compounds comprises those wherein:
$R_{14}$ is $CF_3$, $OCF_3$, or $SF_5$; and $R_{12}$ and $R_{16}$ are chlorine or bromine.

A fourth class of preferred compounds comprises those wherein:
$R_5$ is amino or alkylamino, in which alkyl is optionally substituted with CN, CO—$NH_2$, alkoxycarbonyl, alkoxy, alkylthio, alkylsulfinyl or alkylsulfonyl.

A fifth class of preferred compounds comprises those wherein:
$R_{33}$ is a lone pair of electrons or oxygen;
$R_{31}$ is amino; alkyl optionally substituted by one or more $R_{35}$; phenyl optionally substituted by $R_{36}$ or $R_{37}$; $R_{38}$; NH—CO—NH—N=$CR_8R_9$; NH—CS—NH—N=$CR_8R_9$; NH—CO—$NR_8R_9$; NH—CS—$NR_8R_9$; NH—CO—$OR_8$; or NH—CS—$OR_8$;

Compounds which are particularly valuable in the invention are compounds wherein $R_{12}=R_{16}$=Cl; $R_{13}=R_{15}$=H; $R_{14}=CF_3$; $R_5=NH_2$; $R_{32}=CH_3$; $R_{33}$ is a lone electron pair and $R_4$ and $R_{31}$ are according the following table:

| $R_4$ | $R_{31}$ |
|---|---|
| $SOCH_3$ | $CH_3$ |
| $SOCH_3$ | Et |
| $SOCH_3$ | $CH_2CH_2CH_3$ |

-continued

| $R_4$ | $R_{31}$ |
|---|---|
| $SOCH_3$ | $CH_2CH_2CH_2CH_3$ |
| $SOCH_3$ | $CH_2CH=CH_2$ |
| [001b]$SOCH_3$ | $CH_2CH_2Ph$ |
| $SOCH_3$ | $CH_2CH_2CN$ |
| $SOCH_3$ | $CH_2CH_2C(O)NH_2$ |
| $SOCH_3$ | $CH_2C(O)CH_3$ |
| $SOCH_3$ | $CH_2C(O)OCH_3$ |
| $SOCH_3$ | $CH_2CH_2COOCH_3$ |
| $SOCH_3$ | $CH_2CH_2COOH$ |
| $SOCH_3$ | $CH_2C(O)OC_2H_5$ |
| $SOCH_3$ | $CH_2OCH_3$ |
| $SOCH_3$ | $CH_2CH_2SOCH_3$ |
| $SOCH_3$ | $CH_2CH_2SCH_3$ |
| $SOCH_3$ | $CH_2CH_2S(O)_2CH_3$ |
| $SOCH_3$ | $CH_2CH_2NH_2$ |
| $SOCH_3$ | $CH_2CH_2NO_2$ |
| $SOCH_3$ | $CH_2CH_2COOC_2H_5$ |
| $SOCH_3$ | $CH(CH_3)CH_2COOH$ |
| $SOCH_3$ | $CH_2COOH$ |
| $SCH_3$ | $CH_2COOH$ |
| $S(O)Et$ | $CH_2COOH$ |
| $S(O)_2Et$ | $CH_2COOH$ |
| $SEt$ | $CH_2COOH$ |
| $SOCH_3$ | $CH(CH_3)COOCH_3$ |
| $SOCH_3$ | $CH(COOCH_3)CH_2CONH_2$ |
| $SOCH_3$ | $CH(COOCH_3)CH_2COOH$ |
| $SOCH_3$ | $CH(COOCH_3)CH_2SCH_3$ |
| $SOCH_3$ | $CH(COOH)CHCH_2CH_2COOCH_3$ |
| $SOCH_3$ | $CH(COOH)CHCH_2CH_2CONH_2$ |
| $SOCH_3$ | $CH_2CH_2$-4-imidazole |
| $SOCH_3$ | $CH(COOCH_3)$-4-imidazole |
| $SOCH_3$ | $CH(COOC_2H_5)CH(CH_3)CH_2—C_2H_5$ |
| $SOCH_3$ | $CH(COOC_2H_5)CH_2CH(CH_3)_2$ |
| $SOCH_3$ | $(CH_2)_4CH(NH_2)COOH$ |
| $SOCH_3$ | $CH(COOH)CH_2CH_2SCH_3$ |
| $SOCH_3$ | $CH(COOH)(CH_2)_3CH_3$ |
| $SOCH_3$ | $CH(COOCH_3)CH_2CH_2CH_3$ |
| $S(O)_2CH_3$ | $CH(COOCH_3)CH_2CH_2CH_3$ |
| $SOCH_3$ | $CH_2(CH_2)_4CH(NH_2)COOCH_3$ |
| $SOCH_3$ | $CH_2(CH_2)_3CH(NH_2)(COOCH_3)$ |
| $SOCH_3$ | $C(COOCH_3)(SH)CH(CH_3)_2$ |
| $SOCH_3$ | $CH(COOH)CH_2C_6H_5$ |
| $SOCH_3$ | $CH(COOCH_3)CH_2OH$ |
| $SOCH_3$ | $CH(COOCH_3)(OH)CHCH_3$ |
| $SOCH_3$ | $CH(COOC_2H_5)CH_2C_6H_4(4\text{-}OH)$ |
| $SOCH_3$ | $CH(COOCH_3)CH(CH_3)_2$ |
| $SOCH_3$ | $(CH_2)_4COOH$ |
| $SOCH_3$ | $(CH_2)_5COOH$ |
| $SOCH_3$ | $N(CH_3)_2$ |
| $SOCH_3$ | $P(O)(OCH_3)_2$ |
| $SOCH_3$ | $CH_2CH_2S(O)_2CH_3$ |
| $SOCH_3$ | $NO_2$ |
| $SOCH_3$ | $NHCH_2C_6H_5$ |
| $SOCH_3$ | $NHCH_2CH=CH_2$ |
| $SOCH_3$ | $NHCH_2C\equiv CH$ |
| $SOCH_3$ | $CH_2CH_2CH_2CH_3$ |
| $SOCH_3$ | -cyclohexylamine |
| $SOCH_3$ | $CH_2CH(OH)CH_3$ |
| $SOCH_3$ | 2-pyridyl |
| $SCH_3$ | 2-pyridyl |
| $S(O)Et$ | 2-pyridyl |
| $S(O)_2Et$ | 2-pyridyl |
| $SEt$ | 2-pyridyl |
| $SOCH_3$ | 3-pyridyl |
| $SOCH_3$ | 4-pyridyl |
| $SO_2CH_3$ | 2-pyridyl |
| $SOCH_3$ | 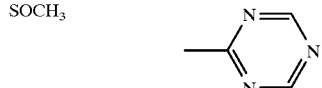 |

-continued

| R₄ | R₃₁ |
|---|---|
| SO₂CH₃ | 4-methyl-1,3,5-triazinyl |
| SOCH₃ | 5-methyl-2-methoxypyridinyl |
| SOCH₃ | 6-methyl-3-carboxamidopyridazinyl |
| SOCH₃ | 4-(C(O)NH₂)phenyl |
| SOCH₃ | 3-(C(O)NH₂)phenyl |
| SOCH₃ | 4-(N(CH₃)C(O)CH₃)phenyl |
| SOCH₃ | 3-(CH₂OH)phenyl |
| SOCH₃ | 2-methylthiazolyl |
| SOCH₃ | 5-methyl-1,3,4-thiadiazolyl |
| SOCH₃ | 3-methyl-1,2,4-triazinyl |
| SOCH₃ | 3-pyridyl-CH₂— |

-continued

| R₄ | R₃₁ |
|---|---|
| SCH₃ | 3-pyridyl-CH₂— |
| S(O)Et | 3-pyridyl-CH₂— |
| S(O)₂Et | 3-pyridyl-CH₂— |
| SEt | 3-pyridyl-CH₂— |
| SOCH₃ | 2-pyridyl-CH₂— |
| SOCH₃ | 4-pyridyl-CH₂— |
| SOCH₃ | 4-(CH₂OH)phenyl-CH₂— |
| SOCH₃ | 4-OH-phenyl |
| SOCH₃ | 4-(S(O)CH₃)phenyl |
| SOCH₃ | 4-(S(O)₂CH₃)phenyl |

-continued

| $R_4$ | $R_{31}$ |
|---|---|
| $SCH_3$ | 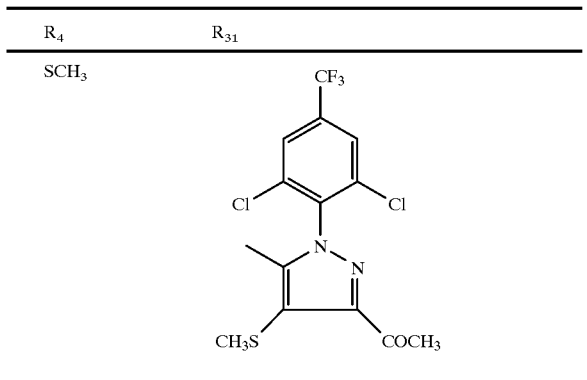 |

Compounds of the general formula (I) can be prepared by reacting the compounds of the general formula (II)

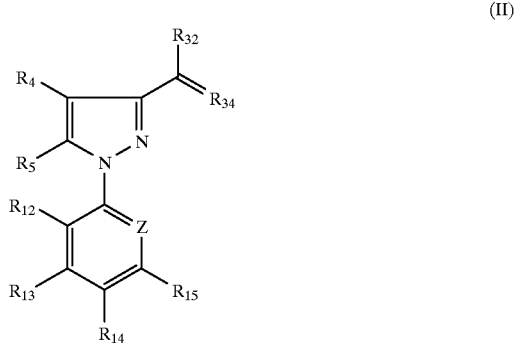
(II)

wherein $R_{34}$ is an oxygen atom, with an appropriate amine of general formula (III): $R_{31}$—$NH_2$. Thus obtained compounds are those of formula (I) wherein $R_{33}$ is a lone electron pair.

This transformation is essentially a dehydration which may be preferably run in the presence of a solvent. The reaction temperature to achieve the transformation can range from about −78° C. to about 200° C., preferably between about −20° C. and about 120° C. Catalysts such as dehydrating agents may be helpful. Among the possible dehydrating agents, one can mention bases or acids or molecular sieves.

The reaction can be conducted in a variety of solvents including but not limited to organic aromatic solvents, such as benzene, toluene, xylene; alcohols, such as methanol, ethanol, isopropanol, ethylene glycol, propylene glycol; ethers, such as tetrahydrofuran, ethyl ether, dimethoxyethane, diglyme, dioxane, crown ethers; halogenated hydrocarbons, such as methylene chloride, chloroform; amides, such as dimethylformamide; ketones, such as acetone. The reaction can also be conducted in a mixed solvent. Azeotropic removal of water is often helpful when possible.

Examples of catalysts for use in the above transformation include alkaline metal hydroxides and trialkylamines as well as inorganic and organic acid catalysts. Examples of the latter two catalysts are hydrochloric acid and p-toluenesulfonic acid.

Compounds of formula (II) wherein $R_{34}$ is oxygen may be prepared from compounds of formula (IV)

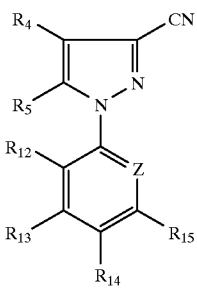
(IV)

by reaction with a Grignard reagent comprising an organomagnesium compound of the formula $R_{31}$—Mg-X wherein X is a halogen atom, preferably chlorine or bromine or iodine. Chlorine is most preferred. The reaction is run in a liquid solvent (such as an ether, a haloalkane, an aromatic solvent, an amide, or a mixture thereof) at a temperature in the range of from about −70° C. to about 150° C. depending on the exact reactant and solvent.

Reactants of formula (IV) may be prepared according to the methods described in the prior art hereinabove cited.

Compounds of formula (I) wherein $R_{33}$ is an oxygen or sulfur atom can be prepared from a compound of formula (II) by reaction with an amine of the formula $R_{31}$—NHOH or $R_{31}$—NHSH, which provides directly the corresponding compound of formula (I) wherein $R_{33}$ is oxygen or sulfur. The reaction may be conducted in a liquid organic solvent at a temperature in the range of from about −30° C. to about 150° C.

The compounds of the formula $R_{31}$—NHOH or $R_{31}$—NHSH are known in the art or can be made according the knowledge of the man skilled in the art.

The formation of the iminium salts in the case in which $R_{33}$ is alkyl or $R_{33}$ and $R_{31}$ together form a divalent group can be achieved by reaction of a ketone or thioketone with a secondary amine under conditions similar to that described hereinabove for the general process.

In the many transformations hereinabove described, it is apparent that selected substituents may occasionally interfere in the contemplated reactions. Such undesired effects can be avoided by using appropriate protecting groups to prevent the unwanted side reactions. It is also possible to use reagents that do not affect functional groups other than those desired to be changed. The particular choice of the appropriate protecting groups and reagents will be easily understood by those skilled in the art.

The use of Chemical Abstracts and of all the available or computerized data banks is considered and suggested as part of the knowledge of the person skilled in the art to choose the proper way of working in the various techniques described in the instant specification.

In order to further illustrate the present invention and the advantages thereof, the following specific examples are given, it being understood that these examples are for the purpose of illustration only and in no way limit the scope of the invention.

EXAMPLE 1

Preparation of N-Phenyl-5-amino-1-[2,6-dichloro-4-(trifluoromethyl)phenyl]-4-methylsulfinyl-1H-pyrazol-3-yl)ethanimine (Compound No. 6):

A stirred mixture of 3-acetyl-5-amino-1-[2,6-dichloro-4-(trifluoromethyl)phenyl]-4-methylsulfinyl-1H-pyrazole (1.0 g, 2.5 mmol), p-toluenesulfonic acid (47.5 mg, 0.25 mmol), aniline (232.5 mg, 2.5 mmol) and benzene (20 ml) was heated 15 h to reflux with removal of water. The mixture was evaporated, then chromatographed so as to give 360 mg of Compound No. 6 (melting point about 179° C.).

EXAMPLE 2

Preparation of N-(2,4-Dichlorophenyl)-[5-amino-1-(2,6-dichloro-4-trifluoromethyl)phenyl-4-methylsulfinyl-1H-pyrazol-3-yl]ethanimine (Compound No. 41):

A mixture of 3-acetyl-5-amino-1-[2,6-dichloro-4-(trifluoromethyl)phenyl]-4-methylsulfinyl-1H-pyrazole (100 mg, 0.25 mmol), titanium tetrachloride (0.25 ml, 0.25 mmol), 2,4-dichloroaniline (202 mg, 1.25 mmol), triethylamine (0.104 ml, 0.75 mmol) and methylene chloride (2 ml) was stirred 12 h at 20° C. The mixture was chromatographed so as to give 80 mg of Compound No. 41 (melting point 83° C.).

EXAMPLE 3

Preparation of N-(Methoxycarbonylamino)-[5-amino-1-(2,6-dichloro-4-trifluoromethyl)phenyl-4-methylsulfinyl-1H-pyrazol-3-yl]ethanimine (Compound No. 2):

A mixture of 3-acetyl-5-amino-1-[2,6-dichloro-4-(trifluoromethyl)phenyl]-4-methylsulfinyl-1H-pyrazole (1 g, 2.5 mmol), methoxycarbonylhydrazine (0.236 g, 2.625 mmol) and methanol (10 ml) was stirred 2 days at 20° C. The mixture was evaporated, then chromatographed so as to give 536 mg of Compound No. 2 as a white powder (m.p. about 121° C.).

EXAMPLE 4

Preparation of N-Methyl-[5-amino-1-[2,6-dichloro-4-(trifluoromethyl)phenyl]-4-methylsulfinyl-1H-pyrazol-3-yl]ethanimine N-oxide (Compound No. 4):

A mixture of 2.0 grams (0.005 mole) of 3-acetyl-5-amino-1-[2,6-dichloro-4-(trifluoromethyl)phenyl]-4-methylsulfinyl-1H-pyrazole, 0.83 gram (0.01 mole) of N-methylhydroxylamine hydrochloride, 1.21 ml (0.015 mole) of pyridine and 150 ml of methanol was stirred 68 h at 20° C. The mixture was successively evaporated, washed with $CH_2Cl_2$ and water; filtered; washed in hot acetonitrile, acetone, hot methanol; and dried so as to give 0.79 gram of Compound No. 4 (m.p. about 228° C.).

EXAMPLE 5

Preparation of N-[[[1-[[5-Amino-1-[2,6-dichloro-4-(trifluoromethyl)phenyl]-4-(methylthio)-1H-pyrazol-3-yl]]ethylidene]]]-4-(methylthio)-3-[1-(phenylamino)ethyl]-1H-pyrazole-5-amine (Compound No. 22):

A stirred mixture of the product of Example 1 (2.5 g, 5.5 mmol) in methanol (25 ml) was treated with sodium borohydride (0.41 g, 11 mmol) at room temperature. Methanol was removed under reduced pressure and the residue was partitioned between methylene chloride and water. The resulting organic phase was dried over sodium sulfate, filtered, concentrated and purified by column chromatography to provide 77 mg of Compound No. 22 (melting point about 189° C.).

The compounds of Table I below generally can be prepared by adaptation of the methods of the foregoing Examples and by modifications thereto as understood by the man skilled in the art. Where there is no melting point (m.p.) provided, the compounds were characterized by mass spectrometry.

TABLE I

The compounds of Table (I) have the general formula (E = lone pair of electrons):

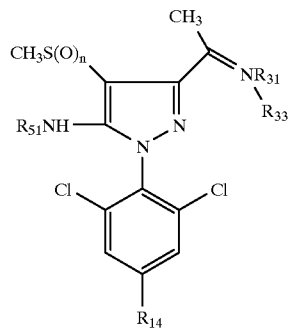

| Compound | $R_{31}$ | $R_{33}$ | n | $R_{51}$ | $R_{14}$ | m.p. ° C. |
|---|---|---|---|---|---|---|
| 1 | $NH_2$ | E | 1 | H | $CF_3$ | 212 |
| 2 | $NHC(O)OCH_3$ | E | 1 | H | $CF_3$ | 121 |
| 3 | H | E | 1 | H | $CF_3$ | 180 |
| 4 | $CH_3$ | O | 1 | H | $CF_3$ | 228 |
| 5 | $NHC(O)NH_2$ | E | 1 | H | $CF_3$ | 114 |
| 6 | Phenyl | E | 1 | H | $CF_3$ | 179 |
| 7 | $CH_2CH_2OH$ | E | 1 | H | $CF_3$ | 93 |

TABLE I-continued

The compounds of Table (I) have the general formula (E = lone pair of electrons):

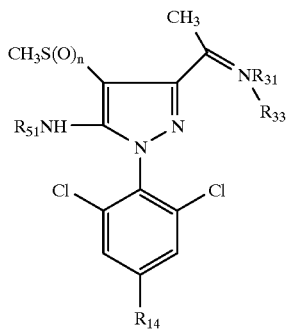

| Compound | $R_{31}$ | $R_{33}$ | n | $R_{51}$ | $R_{14}$ | m.p. °C. |
|---|---|---|---|---|---|---|
| 8 | (2,6-Cl$_2$-4-CF$_3$-C$_6$H$_2$)-N(pyrazole structure with CH$_3$S, COCH$_3$, CH$_3$) | E | 0 | H | CF$_3$ | oil |
| 9 | CH$_3$ | O | 0 | H | CF$_3$ | 196 |
| 10 | CH$_3$ | O | 2 | H | CF$_3$ | 240 |
| 11 | CH$_3$ | O | 1 | CH$_3$ | CF$_3$ | 155 |
| 12 | 4-(OCH$_3$)C$_6$H$_4$ | O | 1 | H | CF$_3$ | oil |
| 13 | CH$_3$ | O | 1 | H | SF$_5$ | oil |
| 14 | NHC(O)NHN=C(CH$_3$)$_2$ | E | 1 | H | CF$_3$ | 209 |
| 15 | NHC(O)NHNH$_2$ | E | 1 | H | CF$_3$ | 197 |
| 16 | 3-(OCH$_3$)C$_6$H$_4$ | E | 1 | H | CF$_3$ | 95 |
| 17 | 4-ClC$_6$H$_4$ | E | 1 | H | CF$_3$ | 165 |
| 18 | 3-BrC$_6$H$_4$ | E | 1 | H | CF$_3$ | 176 |
| 19 | 3-NO$_2$C$_6$H$_4$ | E | 1 | H | CF$_3$ | 170 |
| 20 | 3-OH-4-OCH$_3$—C$_6$H$_3$ | E | 1 | H | CF$_3$ | 120 |
| 21 | NHC(S)NHN=C(CH$_3$)$_2$ | E | 1 | H | CF$_3$ | 200 |
| 22 | (2,6-Cl$_2$-4-CF$_3$-C$_6$H$_2$)-pyrazole with CH$_3$S, CH$_3$, CH(CH$_3$)NH-C$_6$H$_5$ | E | 0 | H | CF$_3$ | 189 |
| 23 | (3-OCH$_3$)(5-OCH$_3$)C$_6$H$_3$ | E | 1 | H | CF$_3$ | 70 |
| 24 | 4-NO$_2$C$_6$H$_4$ | E | 1 | H | CF$_3$ | oil |
| 25 | 3-CNC$_6$H$_4$ | E | 1 | H | CF$_3$ | 95 |
| 26 | 4-CNC$_6$H$_4$ | E | 1 | H | CF$_3$ | 131 |
| 27 | 3-SCH$_3$C$_6$H$_4$ | E | 1 | H | CF$_3$ | 107 |
| 28 | 3,4-Cl$_2$C$_6$H$_3$ | E | 1 | H | CF$_3$ | 172 |
| 29 | 3,5-Cl$_2$C$_6$H$_3$ | E | 1 | H | CF$_3$ | 172 |
| 30 | 4-F-C$_6$H$_4$ | E | 1 | H | CF$_3$ | 191 |
| 31 | CH$_2$COOCH$_3$ | E | 1 | H | CF$_3$ | oil |
| 32 | 3-ClC$_6$H$_4$ | E | 1 | H | CF$_3$ | 162 |

TABLE I-continued

The compounds of Table (I) have the general formula (E = lone pair of electrons):

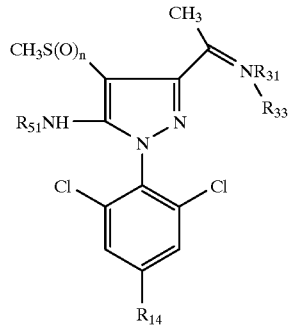

| Compound | $R_{31}$ | $R_{33}$ | n | $R_{51}$ | $R_{14}$ | m.p. °C. |
|---|---|---|---|---|---|---|
| 33 | $2\text{-FC}_6\text{H}_4$ | E | 1 | H | $CF_3$ | 163 |
| 34 | $4\text{-CF}_3\text{C}_6\text{H}_4$ | E | 1 | H | $CF_3$ | 156 |
| 35 | $CH_2Ph$ | E | 1 | H | $CF_3$ | 188 |
| 36 | $3\text{-FC}_6\text{H}_4$ | E | 1 | H | $CF_3$ | 175 |
| 37 | $4\text{-CH}_3\text{C}_6\text{H}_4$ | E | 1 | H | $CF_3$ | 85 |
| 41 | $(2,4\text{-Cl}_2)\text{C}_6\text{H}_3$ | E | 1 | H | $CF_3$ | 183 |
| 42 | $(3\text{-CH}_3)\text{C}_6\text{H}_4$ | E | 1 | H | $CF_3$ | 166 |
| 43 | $(2,4\text{-F}_2)\text{C}_6\text{H}_3$ | E | 1 | H | $CF_3$ | 179 |
| 44 | $(3,4\text{F}_2)\text{C}_6\text{H}_3$ | E | 1 | H | $CF_3$ | 186 |
| 45 | $(2\text{-CH}_3\text{-}4\text{-F})\text{C}_6\text{H}_3$ | E | 1 | H | $CF_3$ | oil |
| 46 | $CH_2\text{-(2-tetrahydrofuran)}$ | E | 1 | H | $CF_3$ | 90 |
| 47 | $CH_2\text{-(2-furan)}$ | E | 1 | H | $CF_3$ | 88 |
| 48 | $CH_2CH=CH_2$ | E | 1 | H | $CF_3$ | 134 |
| 49 | $(2\text{-CH}_3)\text{C}_6\text{H}_4$ | E | 1 | H | $CF_3$ | 72 |
| 50 | $C_6H_5$ | E | 2 | H | $CF_3$ | 186 |
| 51 | $(2\text{-Cl-4-S(O)}_2\text{CH}_3)\text{C}_6\text{H}_3$ | E | 2 | H | $CF_3$ | |
| 52 | $(2\text{-Cl-4-Br})\text{C}_6\text{H}_3$ | E | 1 | H | $CF_3$ | 175 |
| 53 | $(2\text{-F-4-Br})\text{C}_6\text{H}_3$ | E | 1 | H | $CF_3$ | 174 |
| 54 | $(2\text{-Br-4-F})\text{C}_6\text{H}_3$ | E | 1 | H | $CF_3$ | 187 |
| 55 | $(2\text{-Cl-5-CF}_3)\text{C}_6\text{H}_3$ | E | 1 | H | $CF_3$ | 182 |
| 56 | $(2\text{-F-4-Cl})\text{C}_6\text{H}_3$ | E | 1 | H | $CF_3$ | 183 |
| 57 | $(2\text{-Cl-4-F})\text{C}_6\text{H}_3$ | E | 1 | H | $CF_3$ | 184 |
| 58 | $(2\text{-CF}_3\text{-4-Cl})\text{C}_6\text{H}_3$ | E | 1 | H | $CF_3$ | 193 |
| 59 | $(2,4,6\text{-F}_3)\text{C}_6\text{H}_2$ | E | 1 | H | $CF_3$ | 186 |
| 60 | $(4\text{-CF}_3)\text{C}_6\text{H}_4$ | E | 1 | H | $CF_3$ | 75 |
| 61 | $(2,4\text{-F}_2\text{-6-Br})\text{C}_6\text{H}_2$ | E | 1 | H | $CF_3$ | 164 |
| 62 | $(3,5\text{-F}_2)\text{C}_6\text{H}_3$ | E | 1 | H | $CF_3$ | 198 |
| 63 | $(2,3\text{-diCF}_3\text{-4-Cl})\text{C}_6\text{H}_2$ | E | 1 | H | $CF_3$ | 178 |
| 65 | $(3\text{-CF}_3\text{-5-OCH}_3)\text{C}_6\text{H}_3$ | E | 1 | H | $CF_3$ | 96 |
| 66 | $(3\text{-F-4-OCH}_3)\text{C}_6\text{H}_3$ | E | 1 | H | $CF_3$ | 98 |
| 67 | $(2\text{-Br-4-Cl})\text{C}_6\text{H}_3$ | E | 1 | H | $CF_3$ | 174 |
| 68 | $(3\text{-Cl-4-Br})\text{C}_6\text{H}_3$ | E | 1 | H | $CF_3$ | 132 |
| 69 | $(2,6\text{-Cl-4-Br})\text{C}_6\text{H}_2$ | E | 1 | H | $CF_3$ | 213 |
| 70 | $(3,5\text{-Cl}_2\text{-4-Br})\text{C}_6\text{H}_2$ | E | 1 | H | $CF_3$ | 137 |
| 71 | $CH_2\text{-(4-Cl}\text{—}C_6H_4)$ | E | 1 | H | $CF_3$ | |
| 73 | $CH_2(2,4\text{-Cl}_2\text{—}C_6H_3)$ | E | 1 | H | $CF_3$ | |
| 74 | $CH_2\text{-(2-OC}_2\text{H}_5\text{—}C_6H_4)$ | E | 1 | H | $CF_3$ | |
| 75 | $CH_2\text{-(2-F-}C_6H_4)$ | E | 1 | H | $CF_3$ | |
| 76 | $CH_2\text{-(3-F-}C_6H_4)$ | E | 1 | H | $CF_3$ | |
| 77 | $CH_2\text{-(4-F-}C_6H_4)$ | E | 1 | H | $CF_3$ | |
| 78 | $CH_2\text{-(4-OCH}_3\text{—}C_6H_4)$ | E | 1 | H | $CF_3$ | |
| 79 | $CH(CH_3)\text{—}C_6H_5$ | E | 1 | H | $CF_3$ | |
| 80 | $CH_2\text{-(2-CH}_3\text{—}C_6H_4)$ | E | 1 | H | $CF_3$ | |
| 81 | $CH_2\text{-(3-CH}_3\text{—}C_6H_4)$ | E | 1 | H | $CF_3$ | |
| 82 | $CH_2\text{-(4-CH}_3\text{—}C_6H_4)$ | E | 1 | H | $CF_3$ | |
| 83 | $CH_2\text{-(2-CF}_3\text{—}C_6H_4)$ | E | 1 | H | $CF_3$ | |
| 84 | $CH_2\text{-(4-CF}_3\text{—}C_6H_4)$ | E | 1 | H | $CF_3$ | |
| 85 | $CH_2\text{-(3-CF}_3\text{—}C_6H_4)$ | E | 1 | H | $CF_3$ | |
| 86 | $(4\text{-Br})C_6H_4$ | E | 1 | H | $CF_3$ | |
| 87 | $(2,4\text{-dinitro-6-Br})C_6H_2$ | E | 1 | H | $CF_3$ | |
| 88 | $(4\text{-NHC(O)CH}_3)C_6H_4$ | E | 1 | H | $CF_3$ | |
| 89 | $(2\text{-Cl-4-S(O)2CH}_3)C_6H_3$ | E | 1 | H | $CF_3$ | 155 |
| 90 | $(2\text{-NO}_2\text{-4-OCH}_3)C_6H_3$ | E | 1 | H | $CF_3$ | 131 |
| 91 | $(3\text{-CH}_3\text{-4-Cl})C_6H_3$ | E | 1 | H | $CF_3$ | 189 |
| 92 | Cyclopropyl | E | 1 | H | $CF_3$ | 207 |
| 93 | $(2,5\text{-Cl}_2)C_6H_3$ | E | 1 | H | $CF_3$ | 172 |

TABLE I-continued

The compounds of Table (I) have the general formula (E = lone pair of electrons):

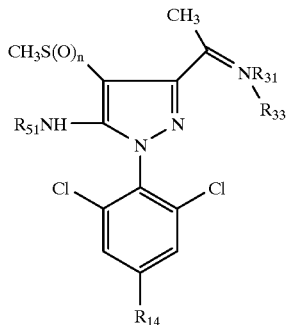

| Compound | $R_{31}$ | $R_{33}$ | n | $R_{51}$ | $R_{14}$ | m.p. °C. |
|---|---|---|---|---|---|---|
| 94 | $(2,4\text{-}CH_3\text{-}6\text{-}NO_2)C_6H_2$ | E | 1 | H | $CF_3$ | 185 |
| 95 | $(3\text{-}Cl\text{-}4\text{-}CN)C_6H_3$ | E | 1 | H | $CF_3$ | |
| 96 | $(4\text{-}OCH_3)C_6H_4$ | E | 2 | H | $CF_3$ | 80 |
| 97 | $(3\text{-}OH\text{-}4\text{-}OCH_3)C_6H_3$ | E | 2 | H | $CF_3$ | 102 |
| 98 | $(2\text{-}SCH_3)C_6H_4$ | E | 1 | H | $CF_3$ | 191 |
| 99 | $(3\text{-}NO_2)C_6H_4$ | E | 2 | H | $CF_3$ | 195 |
| 100 | $(2\text{-}Br\text{-}4\text{-}CF_3\text{-}6\text{-}NO_2)C_6H_2$ | E | 1 | H | $CF_3$ | 115 |
| 101 | $(2\text{-}NO_2\text{-}4\text{-}CH_3)C_6H_3$ | E | 1 | H | $CF_3$ | 145 |
| 102 | $(4\text{-}Cl)C_6H_4$ | E | 2 | H | $CF_3$ | 191 |
| 103 | $(3\text{-}CF_3\text{-}5\text{-}OCH_3)C_6H_3$ | E | 1 | H | $CF_3$ | |
| 104 | $(3,4\text{-}Cl_2)C_6H_3$ | E | 2 | H | $CF_3$ | 188 |
| 105 | pyrazol-3-yl | E | 1 | H | $CF_3$ | |
| 106 | pyridin-2-yl | E | 1 | H | $CF_3$ | |
| 107 | pyridin-4-yl | E | 1 | H | $CF_3$ | |
| 108 | pyrimidin-2-yl | E | 1 | H | $CF_3$ | |
| 109 | quinolin-3-yl | E | 1 | H | $CF_3$ | |
| 110 | thiazol-2-yl | E | 1 | H | $CF_3$ | |
| 111 | (2,4-dimethyl-6-chloropyrimidin-5-yl) | E | 1 | H | $CF_3$ | |

TABLE I-continued

The compounds of Table (I) have the general formula (E = lone pair of electrons):

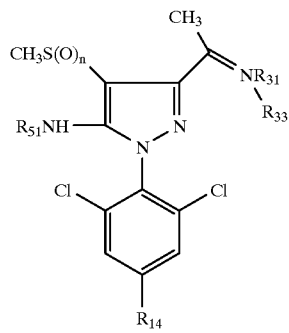

| Compound | $R_{31}$ | $R_{33}$ | n | $R_{51}$ | $R_{14}$ | m.p. °C. |
|---|---|---|---|---|---|---|
| 112 | 4-cyano-5-methylimidazol-2-yl | E | 1 | H | $CF_3$ | |
| 113 | 1,1-dicyanoethyl | E | 1 | H | $CF_3$ | |
| 115 | benzothiazol-2-yl | E | 1 | H | $CF_3$ | |
| 116 | quinolin-3-yl | E | 1 | H | $CF_3$ | |
| 117 | 3-$OCH_3$-5-$CF_3$—$C_6H_3$ | E | 1 | H | $CF_3$ | |
| 118 | 3-Cl-5-Cl—$C_6H_3$ | E | 2 | H | $CF_3$ | 188 |
| 119 | 4-$C_6H_5O$—$C_6H_4$ | E | 2 | H | $CF_3$ | 196 |
| 120 | 4-$C_6H_5NHC_6H_4$ | E | 2 | H | $CF_3$ | 85 |
| 121 | 3-C(O)$NH_2$—$C_6H_4$ | E | 1 | H | $CF_3$ | |
| 122 | 6-methoxypyridin-3-yl | E | 1 | H | $CF_3$ | |
| 123 | thiazolin-5-yl | E | 1 | H | $CF_3$ | |
| 124 | 1,3,4-thiadiazol-2-yl | E | 1 | H | $CF_3$ | |
| 125 | pyridin-3-yl | E | 1 | H | $CF_3$ | 167 |

TABLE I-continued

The compounds of Table (I) have the general formula (E = lone pair of electrons):

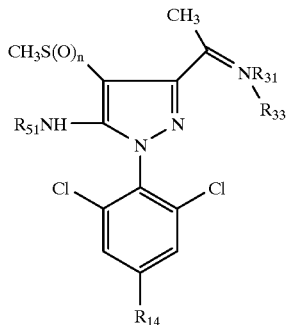

| Compound | $R_{31}$ | $R_{33}$ | n | $R_{51}$ | $R_{14}$ | m.p. °C. |
|---|---|---|---|---|---|---|
| 126 | 4-pyridyl | E | 1 | H | $CF_3$ | |
| 127 | $CH_2CH_2C(O)OCH_3$ | E | 1 | H | $CF_3$ | 69 |
| 128 | $CH_2C{\equiv}CH$ | E | 1 | H | $CF_3$ | 127 |
| 129 | $(CH_2)_5CH_3$ | E | 1 | H | $CF_3$ | 114 |
| 130 | $(CH_2)_4CH_3$ | E | 1 | H | $CF_3$ | 132 |
| 131 | $(CH_2)_3CH_3$ | E | 1 | H | $CF_3$ | 131 |
| 132 | $CH(CH_3)_2$ | E | 1 | H | $CF_3$ | 194 |
| 133 | $CH_2CH_2CH_3$ | E | 1 | H | $CF_3$ | 129 |
| 134 | $(CH_2)_6CH_3$ | E | 1 | H | $CF_3$ | 108 |
| 135 | $(CH_2)_7CH_3$ | E | 1 | H | $CF_3$ | 124 |
| 136 | $(CH_2)_8CH_3$ | E | 1 | H | $CF_3$ | 125 |
| 137 | $(CH_2)_9CH_3$ | E | 1 | H | $CF_3$ | 83 |
| 138 | $(CH_2)_8CH{=}CH(CH_2)_7CH_3$ | E | 1 | H | $CF_3$ | |
| 139 | $(CH_2)_{17}CH_3$ | E | 1 | H | $CF_3$ | 64 |
| 140 | $(CH_2)_{11}CH_3$ | E | 1 | H | $CF_3$ | |
| 141 | $(CH_2)_{13}CH_3$ | E | 1 | H | $CF_3$ | |
| 142 | $(CH_2)_{10}CH_3$ | E | 1 | H | $CF_3$ | |
| 143 | $CH_2CH(CH_3)_2$ | E | 1 | H | $CF_3$ | 179 |
| 144 | $CH_2CH_2CH(CH_3)_2$ | E | 1 | H | $CF_3$ | 138 |
| 145 | $CH_2CH(CH_3)CH_2CH_3$ | E | 1 | H | $CF_3$ | 150 |
| 146 | $CH(CH_3)CH(CH_3)_2$ | E | 1 | H | $CF_3$ | 178 |
| 147 | $(CH_2)_{12}CH_3$ | E | 1 | H | $CF_3$ | |
| 148 | $(CH_2)_{15}CH_3$ | E | 1 | H | $CF_3$ | 56 |

The following non-limiting examples illustrate the use of the compounds of the invention in controlling pests.

The species tested were as follows:

| GENUS, SPECIES | COMMON NAME |
|---|---|
| Aphis gossypii | cotton leaf aphid |
| Musca domestica | housefly |
| Diabrotica virgifera | Western corn rootworm |
| Periplaneta americana | American cockroaches |
| Spodoptera eridania | Southern armyworm |
| Schizaphis graminum | greenbug |
| Ctenocephalides felis | Cat flea |
| Rhipicephalus sanguineas | Brown dog tick |

The Soil Drench Test (Systemic Activity)

Cotton and sorghum plants were established in pots. One day prior to treatment, each pot was infested with about 25 aphids of a mixed population. Cotton plants were infested with aphids and sorghum plants were infested with the greenbug. The selected compound of formula (I) was applied to the soil surface in a dilution that delivered the equivalent of 10.0 ppm soil concentration by weight. Aphid counts were obtained at 5 DAT (=days after treatment). The number of aphids on the treated plants was compared to the number of those on the untreated control plants. This test shows systemic activity (migration of the active ingredient).

The Housefly Bait/Contact Test

About 25 four to six-day-old adult houseflies were anesthetized and placed in a cage with a sugar water bait solution containing the compound. The concentration of the selected compound of formula (I) in the bait solution was 50 ppm. After 24 hours, flies which showed no movement on stimulation were considered dead.

Foliar Application (Contact Test) with Aphids

Aphid-infested cotton plants were placed on a revolving turntable, and sprayed to runoff with a 100 ppm formulation of the selected compound of formula (I). The treated, A. gossypii-infested plants were held for three days after treatment, after which the dead aphids were counted.

The obtained results are as follows (In this table 'X' means high activity; '+' means moderate activity; '−' means low activity; and 'NT' means no activity.):

| Compound No. | Systemic activity on aphids | Systemic activity on greenbugs | Activity on house flies by contact | Foliar activity on aphids |
|---|---|---|---|---|
| 1 | + | X | X | X |
| 2 | − | − | X | − |
| 3 | X | X | NT | NT |
| 4 | X | X | X | X |
| 5 | − | − | X | X |
| 6 | X | X | NT | X |
| 7 | + | X | X | X |
| 8 | − | − | X | − |
| 9 | + | X | X | − |
| 10 | − | X | X | − |
| 11 | − | X | X | − |
| 12 | X | X | X | X |
| 13 | − | X | X | − |
| 14 | − | X | X | − |
| 15 | − | X | + | − |
| 16 | X | X | X | + |
| 17 | X | X | X | X |
| 18 | + | X | X | X |
| 19 | X | X | X | − |
| 20 | X | X | X | X |
| 21 | + | + | X | − |
| 22 | − | − | + | X |
| 23 | X | X | X | X |
| 24 | X | X | NT | NT |
| 25 | X | X | X | X |
| 26 | + | X | X | X |
| 27 | + | X | X | X |
| 28 | + | X | X | − |
| 29 | + | X | X | − |
| 30 | + | X | X | − |
| 31 | + | X | X | X |
| 32 | X | X | X | − |
| 33 | + | X | X | X |
| 34 | + | X | X | X |
| 35 | X | X | X | X |
| 36 | X | X | X | − |
| 37 | + | X | X | X |
| 41 | − | − | X | + |
| 42 | + | X | X | X |
| 43 | + | X | X | − |
| 44 | X | X | X | − |
| 45 | + | X | X | + |
| 46 | X | X | X | X |
| 47 | X | X | X | X |
| 48 | + | X | X | X |
| 49 | X | X | X | X |
| 50 | + | X | X | X |
| 51 | X | X | X | − |
| 52 | + | X | X | X |
| 53 | + | X | X | X |
| 54 | + | X | X | − |
| 55 | − | X | X | − |
| 56 | + | X | X | X |
| 57 | − | X | X | X |
| 58 | − | X | X | − |
| 59 | + | X | X | − |
| 60 | X | X | X | X |
| 61 | − | X | X | − |
| 62 | − | X | X | X |
| 63 | X | X | − | X |
| 65 | X | X | X | X |
| 66 | X | X | X | X |
| 67 | + | X | X | − |
| 68 | X | X | X | X |
| 69 | − | X | − | − |
| 70 | X | X | X | X |
| 71 | + | X | X | X |
| 74 | + | X | X | X |
| 75 | X | X | X | X |
| 76 | + | X | X | X |
| 77 | X | X | X | X |
| 78 | X | X | X | X |
| 79 | X | X | X | X |
| 80 | X | X | X | X |
| 81 | X | X | X | X |
| 82 | + | X | X | X |
| 83 | + | X | X | X |
| 84 | X | X | X | X |
| 85 | X | X | X | X |
| 86 | − | + | − | X |
| 87 | NT | NT | − | − |
| 88 | NT | NT | X | X |
| 89 | NT | NT | X | + |
| 90 | + | + | X | − |
| 91 | + | X | X | − |
| 92 | + | X | X | X |
| 93 | NT | NT | − | − |
| 94 | NT | NT | X | − |
| 95 | − | X | NT | NT |
| 96 | + | X | X | NT |
| 97 | + | X | X | NT |
| 98 | + | X | X | − |
| 99 | + | + | X | + |
| 100 | NT | NT | X | − |
| 101 | − | + | X | − |
| 102 | + | X | X | X |
| 103 | NT | NT | − | X |
| 104 | X | X | X | NT |
| 105 | + | X | X | − |
| 106 | NT | NT | X | X |
| 107 | NT | NT | X | − |
| 108 | NT | NT | X | X |
| 109 | NT | NT | X | NT |
| 110 | + | X | X | X |
| 111 | − | + | + | − |
| 112 | NT | NT | X | + |
| 113 | − | X | − | − |
| 115 | + | X | X | X |
| 116 | − | X | X | X |
| 117 | − | − | − | |
| 118 | X | X | X | |
| 119 | X | X | X | X |
| 120 | + | X | X | − |
| 121 | X | X | X | + |
| 122 | X | | X | X |
| 123 | X | X | X | − |
| 124 | X | | X | − |
| 125 | X | | X | X |
| 126 | X | X | X | − |
| 127 | X | | | |
| 128 | X | X | X | − |
| 129 | X | X | X | − |
| 130 | X | X | X | − |
| 131 | X | X | − | |
| 132 | X | X | X | |
| 133 | X | X | − | |
| 134 | − | X | X | − |
| 135 | X | − | X | − |
| 136 | X | X | X | − |
| 137 | X | X | X | − |
| 138 | X | X | X | − |
| 139 | + | X | X | − |
| 140 | X | X | X | − |
| 141 | X | X | X | |
| 142 | X | X | − | |
| 143 | X | X | − | |
| 144 | X | X | − | − |
| 145 | X | X | X | + |
| 146 | + | X | X | X |
| 147 | X | X | − | − |
| 148 | X | X | + | − |

The present invention provides a method for controlling pests at a locus, said method comprising applying to said locus a pesticidally effective amount of a compound of formula (I) or a pesticidally acceptable salt thereof or a composition containing the active ingredient. The method is preferably used for the systemic control of arthropods at a locus, espcially some insects or mites which feed on the above-ground portions of plants. Control of such foliar pests may be provided by direct foliar application or by application by, for example, soil spray or granule application to the plant roots or plant seeds with subsequent systemic translocation to the above-ground portions of the plants. Such systematic activity includes the control of insects which reside not only at the point of application but at a remote part of the plant, for example, by translocation from one side of a leaf to the other or from a treated leaf to an untreated leaf. Examples of the classes of insect pests which may be systemically controlled by the compounds of the invention include the Homoptera order (piercing-sucking), Hemiptera order (piercing-sucking), and Thysanoptera order. The invention is especially appropriate for aphids and thrips.

As is evident from the foregoing pesticidal uses, the present invention provides pesticidally active compounds and methods of use of said compounds for the control of a number of pest species which includes: arthropods, especially insects or mites; plant nematodes; or helminth or protozoan pests. The compounds of formula (I) or pesticidally acceptable salts thereof thus are advantageously employed in practical uses, for example, in agricultural or horticultural crops, forestry, veterinary medicine or livestock husbandry, or in public health. From this point forward, whenever the term "compounds of formula (I)" is used this term embraces compounds of formula (I) and their pesticidally acceptable salts. The term "compound of formula (I)" embraces a compound of formula (I) and a pesticidally acceptable salt thereof.

The present invention therefore provides a method of control of pests at a locus which comprises the treatment of the locus (e.g., by application or administration) with an effective amount of a compound of formula (I) or a pesticidally acceptable salt thereof, wherein the substituent groups are as hereinbefore defined. The locus includes, for example, the pest itself or the place (plant, animal, field, structure, premises, forest, orchard, waterway, soil, plant or animal product, or the like) where the pest resides or feeds.

The compounds of this invention may in addition be used to control soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

Compounds of the invention may be used in the following applications and on the following pests including arthropods, especially insects or mites, nematodes, or helminth or protozoan pests:

In the protection of stored products, for example cereals, including grain or flour, groundnuts, animal feedstuffs, timber or household goods, e.g. carpets and textiles, compounds of the invention are useful against attack by arthropods, more especially beetles, including weevils, moths or mites, for example Ephestia spp. (flour moths), Anthrenus spp. (carpet beetles), Tribolium spp. (flour beetles), Sitophilus spp. (grain weevils) or Acarus spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, Reticulitermes spp., Heterotermes spp., Coptotermes spp.

In agriculture against adults, larvae and eggs of Lepidoptera (butterflies and moths), e.g. Heliothis spp. such as *Heliothis virescens* (tobacco budworm), *Heliothis armigera* and *Heliothis zea*. Against adults and larvae of Coleoptera (beetles) e.g. Anthonomus spp. e.g. grandis (cotton boll weevil), *Leptinotarsa decemlineata* (Colorado potato beetle), Diabrotica spp. (corn rootworms). Against Heteroptera (Hemiptera and Homoptera) e.g Psylla spp., Bemisia spp., Trialeurodes spp., Aphis spp., Myzus spp., *Megoura viciae*, Phylloxera spp., Nephotettix spp. (rice leaf hoppers), Nilaparvata spp.

Against Diptera e.g. Musca spp. Against Thysanoptera such as *Thrips tabaci*. Against Orthoptera such as Locusta and Schistocerca spp. (locusts and crickets) e.g. Gryllus spp., and Acheta spp. for example, *Blatta orientalis, Periplaneta americana, Blatella germanica, Locusta migratoria migratorioides*, and *Schistocerca gregaria*. Against Collembola e.g. Periplaneta spp. and Blattela spp. (roaches). Against Isoptera e.g. Coptotermes spp. (termites).

Against arthropods of agricultural significance such as Acari (mites) e.g. Teiranychus spp., and Panonychus spp.

Against nematodes which attack plants or trees of importance to agriculture, forestry or horticulture either directly or by spreading bacterial, viral, mycoplasma or fungal diseases of the plants. For example root-knot nematodes such as Meloidogyne spp. (e.g. *M. incognita*).

In the field of veterinary medicine or livestock husbandry or in the maintenance of public health against arthropods, helminths or protozoa which are parasitic internally or externally upon vertebrates, particularly warm-blooded vertebrates, for example domestic animals, e.g. cattle, sheep, goats, equines, swine, poultry, dogs or cats, for example Acarina, including ticks e.g. Ixodes spp., Boophilus spp. e.g. *Boophilus microplus*, Rhipicephalus spp. e.g. *Rhipicephalus appendiculatus*, Ornithodorus spp. (e.g. *Ornithodorus moubata*) and mites (e.g. Damalinia spp.); Diptera (e.g Aedes spp., Anopheles spp., Musca spp., Hypoderma spp.); Hemiptera; Dictyoptera (e.g Periplaneta spp., Blatella spp.); Hymenoptera; for example against infections of the gastrointestinal tract caused by parasitic nematode worms, for example members of the family Trichostrongylidae; in the control and treatment of protozoal diseases caused by, for example, Eimeria spp. e.g *Trypanosoms cruzi*, Leishaminia spp., Plasmodium spp., Babesis spp., Trichomonadidae spp., Toxoplasma spp. and Theileria spp.

In practical use for the control of arthropods, especially insects or mites, or nematode pests of plants, a method, for example, comprises applying to the plants or to the medium in which they grow an effective amount of a compound of the invention. For such a method, the active compound is generally applied to the locus in which the arthropod or nematode infestation is to be controlled at an effective rate in the range of about 5 g to about 1 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. More preferably an effective rate range of the active compound is from about 50 g/ha to about 400 g/ha.

When a pest is soil-borne, the active compound generally in a formulated composition, is distributed evenly over the area to be treated (i.e., for example broadcast or band treatment) in any convenient manner and is applied at rates from about 5 to about 1 kg ai/ha, preferably from about 50 to about 250 g ai/ha. When applied as a root dip to seedlings or drip irrigation to plants the liquid solution or suspension contains from about 0.075 to about 1000 mg ai/l, preferably from about 25 to about 200 mg ai/l. Application may be made, if desired, to the field or crop-growing area generally or in close proximity to the seed or plant to be protected from attack. The active component can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting.

The compounds of the invention and methods of control of pests therewith are of particular value in the protection of field, forage, plantation, glasshouse, orchard or vineyard crops, of ornamentals, or of plantation or forest trees, for example: cereals (such as wheat or rice), cotton, vegetables (such as peppers), field crops (such as sugar beets, soybeans or oil seed rape), grassland or forage crops (such as maize or sorghum), orchards or groves (such as of stone or pit fruit or citrus), ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compounds of the invention and methods of use thereof are of particular value in the control of arthropods, helminths or protozoa which are injurious to, or spread or act as vectors of diseases in domestic animals, for example those hereinbefore mentioned, and more especially in the control of ticks, mites, lice, fleas, midges, or biting, nuisance or myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

Furthermore, compounds of the invention may be useful for coccidiosis, a disease caused by infections from protozoan parasites of the genus Eimeria. It is an important potential cause of economic loss in domestic animals and birds, particularly those raised or kept under intensive conditions. For example, cattle, sheep, pigs or rabbits may be affected, but the disease is especially important in poultry, particularly in chickens. Administration of a small amount of a compound of the invention, preferably by a combination with feed is effective in preventing or greatly reducing the incidence of coccidiosis. The compounds are effective against both the cecal form and the intestinal forms. Furthermore, the compounds of the invention may also exert an inhibiting effect on oocytes by greatly reducing the number and sporulation of those produced. The poultry disease is generally spread by the birds picking up the infectious organism in droppings in or on contaminated litter, ground, food, or drinking water. The disease is manifested by hemorrhage, accumulation of blood in the ceca, passage of blood to the droppings, weakness and digestive disturbances. The disease often terminates in the death of the animal, but the fowl which survive severe infections have had their market value substantially reduced as a result of the infection.

The compositions hereinafter described for application to growing crops or crop growing loci or as a seed dressing may, in general, alternatively be employed for topical application to animals or in the protection of stored products, household goods, property or areas of the general environment. Suitable means of applying the compounds of the invention include:

to growing crops as foliar sprays, dusts, granules, fogs or foams or also as suspensions of finely divided or encapsulated compositions as soil or root treatments by liquid drenches, dusts, granules, smokes or foams; to seeds of crops via application as seed dressings by liquid slurries or dusts;

to animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;

to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water;

to domestic animals in feed to control fly larvae feeding in their feces.

In practice, the compounds of the invention most frequently form parts of compositions. These compositions can be employed to control: arthopods, especially insects or mites; nematodes; or heiminth or protozoan pests. The compositions may be of any type known in the art suitable for application to the desired pest in any premises or indoor or outdoor area or by internal or external administration to vertebrates. These compositions contain at least one compound of formula (I) or a pesticidally acceptable salt thereof, such as described earlier, as the active ingredient in combination or association with one or more other compatible components which are for example, solid or liquid carriers or diluents, adjuvants, surface-active agents, or the like appropriate for the intended use and which are agronomically or medicinally acceptable. These compositions, which may be prepared by any manner known in the art, likewise form a part of this invention.

These compositions may also contain other kinds of ingredients such as protective colloids, adhesives, thickeners, thixotropic agents, penetrating agents, spray oils (especially for acaricidal use), stabilizers, preservative agents (especially mold preservatives), sequestering agents, or the like, as well as other known active ingredients with pesticidal properties (particularly insecticidal, miticidal, nematicidal, or fungicidal) or with properties regulating the growth of plants. More generally, the compounds employed in the invention may be combined with all the solid or liquid additives corresponding to the usual techniques of formulation.

Compositions, suitable for applications in agriculture, horticulture, or the like include formulations suitable for use as, for example, sprays, dusts, granules, fogs, foams, emulsions, or the like.

The effective use doses of the compounds employed in the invention can vary within wide limits, particularly depending on the nature of the pest to be eliminated or degree of infestation, for example, of crops with these pests. In general, the compositions according to the invention preferably contain, particularly for agricultural use, about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminum or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or coloring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethylsulfoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Among these are e.g., salts of polyacrylic acids, salts of lignosulfonic acids, salts of phenolsulfonic or naphthalenesulfonic acids, polycondensates of ethylene oxide with fatty alcohols or fatty acids or fatty esters or fatty amines, substituted phenols (particularly alkylphenols or arylphenols), salts of sulfosuccinic acid esters, taurine derivatives (particularly alkyltaurates), phosphoric esters of alcohols or of polycondensates of ethylene oxide with phenols, esters of fatty acids with polyols, or sulfate, sulfonate or phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain other additives such as adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

Compositions containing compounds of formula (I), or pesticidally acceptable salts thereof, which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate, e.g. benomyl and iprodione), bactericides, arthropod or vertebrate attractants or repellents or pheromones, deodorants, flavoring agents, dyes, or auxiliary therapeutic agents, e.g trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with the compositions of the present invention are: acephate, chloropyrifos, demeton-S-methyl, disulfoton, ethoprofos, fenitrothion, fenamiphos, fonofos, isazophos, isofenphos, malathion, monocrotophos, parathion, phorate, phosalone, pirimiphos-methyl, terbufos, triazophos, cyfluthrin, cypermethrin, deltamethrin, fenpropathrin, fenvalerate, permethrin, tefluthrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorvos, diaveridine or dimetriadazole.

For their agricultural application, the compounds of the formula (I), or pesticidally acceptable salts thereof, are therefore generally in the form of compositions, which are in various solid or liquid forms.

Solid forms of compositions which can be used are dusting powders (with a content of the compound of formula (I), or a pesticidally acceptable salt thereof, ranging up to about 80%), wettable powders or granules (including water dispersible granules), particularly those obtained by extrusion, compacting, impregnation of a granular carrier, or granulation starting from a powder (the content of the compound of formula (I), or a pesticidally acceptable salt thereof, in these wettable powders or granules being between about 0.5 and about 80%). Solid homogeneous or heterogeneous compositions containing one or more compounds of formula (I), or pesticidally acceptable salts thereof, for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications, be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (e.g low or ultra-low volume) depending upon the need or application technique. The compounds or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble. Some organic solids or inorganic salts may be dissolved in the carrier to help prevent settling or as antifreezes for water.

The wettable powders (or powders for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. from about 1 to about 20% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod, plant nematode, helminth or protozoan pests usually contain from about 0.00001% to about 95%, more particularly from about 0.0005% to about 50% by weight of one or more compounds of formula (I), or pesticidally acceptable salts thereof, or of total active ingredients (that is to say the compound of formula (I), or a pesticidally acceptable salt thereof, together with: other substances toxic to arthropods or plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more compounds of formula (I) or pesticidally acceptable salts thereof. For administration to animals orally or parenterally, including percutaneously, solid or liquid compositions normally contain from about 0.1% to about 90% by weight of one or more compounds of formula (I) or pesticidally acceptable salts thereof. Medicated feedstuffs normally contain from about 0.001% to about 3% by weight of one or more compounds of formula (I) or pesticidally acceptable salts thereof. Concentrates or supplements for mixing with feedstuffs normally contain from about 5% to about 90%, preferably from about 5% to about 50%, by weight of one or more compounds of formula (I) or pesticidally acceptable salts thereof. Mineral salt licks normally contain from about 0.1% to about 10% by weight of one or more compounds of formula (I) or pesticidally acceptable salts thereof.

Dusts or liquid compositions for application to livestock, goods, premises or outdoor areas may contain from about 0.0001% to about 15%, more especially from about 0.005% to about 2.0%, by weight, of one or more compounds of formula (I) or pesticidally acceptable salts thereof. Suitable concentrations in treated waters are between about 0.0001 ppm and about 20 ppm, more particularly about 0.001 ppm to about 5.0 ppm of one or more compounds of formula (I), or pesticidally acceptable salts thereof, and may be used therapeutically in fish farming with appropriate exposure times. Edible baits may contain from about 0.01% to about 5%, preferably from about 0.01% to about 1.0%, by weight, of one or more compounds of formula (I) or pesticidally acceptable salts thereof.

When administered to vertebrates parenterally, orally or by percutaneous or other means, the dosage of compounds of formula (I), or pesticidally acceptable salts thereof, will depend upon the species, age, or health of the vertebrate and upon the nature and degree of its actual or potential infestation by arthropod, helminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 2A–2M illustrate compositions for use against arthropods, especially mites or insects, plant nematodes, or helminth or protozoan pests which comprise, as active ingredient, compounds of formula (I), or pesticidally acceptable salts thereof, such as those described in the preparative examples. The compositions described in EXAMPLES 2A–2M can each be diluted to give a sprayable composition at concentrations suitable for use in the field. Generic chemical descriptions of the ingredients (for which all of the following percentages are in weight percent), used in the composition EXAMPLES 2A–2M exemplified below, are as follows:

| Trade Name | Chemical Description |
|---|---|
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan No 2 | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

EXAMPLE 2A

A water soluble concentrate is prepared with the composition as follows:

| Active ingredient | 7% |
|---|---|
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

EXAMPLE 2B

An emulsifiable concentrate (EC) is prepared with the composition as follows:

| Active ingredient | 25%(max) |
|---|---|
| Soprophor BSU | 10% |
| Arylan CA | 5% |
| N-methylpyrrolidone | 50% |
| Solvesso 150 | 10% |

The first three components are dissolved in N-methylpyrrolidone and to this is then added the Solvesso 150 to give the final volume.

EXAMPLE 2C

A wettable powder (WP) is prepared with the composition as follows:

| Active ingredient | 40% |
|---|---|
| Arylan S | 2% |
| Darvan No 2 | 5% |
| Celite PF | 53% |

The ingredients are mixed and ground in a hammer-mill to a powder with a particle size of less than 50 microns.

EXAMPLE 2D

An aqueous-flowable formulation is prepared with the composition as follows:

| Active ingredient | 40.00% |
|---|---|
| Ethylan BCP | 1.00% |
| Sopropon T360 | 0.20% |
| Ethylene glycol | 5.00% |
| Rhodigel 230 | 0.15% |
| Water | 53.65% |

The ingredients are intimately mixed and are ground in a bead mill until a mean particle size of less than 3 microns is obtained.

EXAMPLE 2E

An emulsifiable suspension concentrate is prepared with the composition as follows:

| Active ingredient | 30.0% |
|---|---|
| Ethylan BCP | 10.0% |

-continued

| | |
|---|---|
| Bentone 38 | 0.5% |
| Solvesso 150 | 59.5% |

The ingredients are intimately mixed and ground in a beadmill until a mean particle size of less than 3 microns is obtained.

EXAMPLE 2F

A water dispersible granule is prepared with the composition as follows:

| | |
|---|---|
| Active ingredient | 30% |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

EXAMPLE 2G

A dusting powder is prepared with the composition as follows:

| | |
|---|---|
| Active ingredient | 1 to 10% |
| Talc powder-superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

EXAMPLE 2H

An edible bait is prepared with the composition as follows:

| | |
|---|---|
| Active ingredient | 0.1 to 1.0% |
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

EXAMPLE 2I

A solution formulation is prepared with a composition as follows:

| | |
|---|---|
| Active ingredient | 15% |
| Dimethyl sulfoxide | 85% |

The active ingredient is dissolved in dimethyl sulfoxide with mixing and/or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

EXAMPLE 2J

A wettable powder is prepared with the composition as follows:

| | |
|---|---|
| Active ingredient | 50% |
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, helminths or protozoa, by spraying or dipping, or by oral administration in drinking water, to control the arthropods, helminths or protozoa.

EXAMPLE 2K

A slow release bolus composition is formed from granules containing the following components in varying percentages (similar to those described for the previous compositions) depending upon need:

| |
|---|
| Active ingredient |
| Density agent |
| Slow-release agent |
| Binder |

The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods, helminths or protozoa.

EXAMPLE 2L

A slow release composition in the form of granules, pellets, brickettes or the like can be prepared with compositions as follows:

| | |
|---|---|
| Active ingredient | 0.5 to 25% |
| Polyvinyl chloride | 75 to 99.5% |
| Dioctyl phthalate (plasticizer) | |

The components are blended and then formed into suitable shapes by meltextrusion or molding. These composition arc useful, for example, for addition to standing water or for fabrication into collars or eartags for attachment to domestic animals to control pests by slow release.

EXAMPLE 2M

A water dispersible granule is prepared with the composition as follows:

| | |
|---|---|
| Active ingredient | 85%(max) |
| Polyvinylpyrrolidone | 5% |
| Attapulgite clay | 6% |
| Sodium lauryl sulfate | 2% |
| Glycerine | 2% |

The ingredients are mixed as a 45% slurry with water and wet milled to a particle size of 4 microns, then spray-dried to remove water.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A compound having the formula:

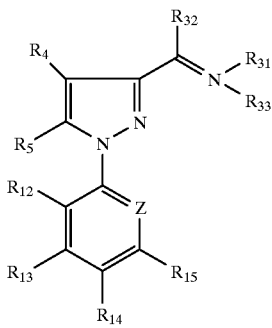

(I)

or a pesticidally acceptable salt thereof, wherein:

$R_{31}$ is H, CN, $NO_2$, NO, SH, $C_1$–$C_6$ alkylthio, $NH_2$, $P(O)(OR_8)(OR_9)$ or $R_{38}$; or $R_{31}$ is mono($C_1$–$C_6$ alkyl)amino, di($C_1$–$C_6$ alkyl)amino, formyl($C_1$–$C_6$ alkyl), $C_1$–$C_{20}$ alkyl, $C_3$–$C_6$ cycloalkyl or $C_4$–$C_8$(cycloalkyl)alkyl, each of which alkyl is optionally substituted by one or more $R_{35}$; or $R_{31}$ is naphthyl or phenyl, each of which is optionally substituted by one or more $R_{36}$ or $R_{37}$; or $R_{31}$ is NH—CO—NH—N=$CR_8R_9$, NH—CS—NH—N=$CR_8R_9$, NH—CO—$NR_8R_9$, NH—CS—$NR_8R_9$, NH—CO—$OR_8$, NH—CS—$OR_8$ or NH—CO—NH—$NH_2$;

$R_{32}$ is $C_1$–$C_6$ alkyl, $C_3$–$C_7$ cycloalkyl or $C_4$–$C_8$ cycloalkylalkyl, each of which alkyl is optionally substituted by one or more $R_{35}$; or $R_{32}$ is phenyl, optionally substituted by one or more $R_{36}$ or $R_{37}$; or $R_{32}$ is $R_{38}$;

$R_{33}$ is a lone pair of electrons; or $R_{33}$ is an oxygen or sulfur atom, linked to the nitrogen atom by a covalent bond or a bond which is partially covalent and partially ionic; or $R_{33}$ is $C_1$–$C_6$ alkyl, the nitrogen atom to which $R_{33}$ is linked then being in the cationic form $N^+$; or $R_{31}$ and $R_{33}$ together form $C_2$–$C_6$ alkylene, wherein one or two of the carbon atoms is each optionally replaced by a heteroatom selected from the group consisting of O, S and N, the nitrogen atom to which $R_{31}$ and $R_{33}$ are linked then being in the cationic form $N^+$;

$R_{35}$ is halogen, amino, $C_1$–$C_6$ alkylamino, di($C_1$–$C_6$ alkyl)amino, $NO_2$, CN, $C_1$–$C_6$ alkoxy, ($C_1$–$C_6$ alkoxy)carbonyl, hydroxycarbonyl, ($C_1$–$C_6$ alkyl)carbonyl, methylene, methylidyne, acetenyl or acetenyl($C_1$–$C_6$ alkyl); or $R_{35}$ is phenyl, optionally substituted by one or more $R_{36}$; or $R_{35}$ is a heterocyclic ring having a total of 3 to 7 ring atoms of which 1 to 4 are heteroatoms selected from the group consisting of O, S and N, said heterocyclic ring being saturated or unsaturated and being optionally substituted by one or more $R_{36}$; or $R_{35}$ is OH, SH, $C_1$–$C_6$ alkylthio, $C_1$–$C_6$ alkylsulfinyl, $C_1$–$C_6$ alkylsulfonyl, aminocarbonyl, ($C_1$–$C_6$) alkylaminocarbonyl, di($C_1$–$C_6$ alkyl)aminocarbonyl, ($C_1$–$C_6$ alkoxy)carbonyl or $P(O)(OR_8)(OR_9)$;

$R_{36}$ is $SF_5$, halogen, $C_1$–$C_6$ alkyl, $C_1$–$C_6$ hydroxyalkyl, $NO_2$, CN, amino, $C_1$–$C_6$ alkylamino, di($C_1$–$C_6$ alkyl)amino, di($C_1$–$C_6$ alkyl)aminocarbonylamino, ($C_1$–$C_6$ alkyl)aminocarbonylamino, aminocarbonylamino, ($C_1$–$C_6$ alkyl)carbonyl, ($C_1$–$C_6$ alkoxy)carbonyl, ($C_1$–$C_6$ alkyl)carbonylamino, ($C_1$–$C_6$ alkoxy)carbonylamino, aminocarbonyl, di($C_1$–$C_6$ alkyl)aminocarbonyl, ($C_1$–$C_6$ alkyl)aminocarbonyl, hydroxycarbonyl, aminocarbonyloxy, ($C_1$–$C_6$ alkyl)aminocarbonyloxy, di($C_1$–$C_6$ alkyl)aminocarbonyloxy, hydroxy, $C_1$–$C_6$ alkoxy, $C_1$–$C_6$ haloalkyl, $C_1$–$C_6$ haloalkoxy, $C_1$–$C_6$ alkylthio, $C_1$–$C_6$ alkylsulfinyl, $C_1$–$C_6$ alkylsulfonyl, $C_1$–$C_6$ haloalkylthio, $C_1$–$C_6$ haloalkylsulfinyl, $C_1$–$C_6$ haloalkylsulfonyl, $P(O)(OR_8)(OR_9)$, ($C_1$–$C_6$ alkyl)[($C_1$–$C_6$ alkyl)carbonyl]amino or phenylamino($C_1$–$C_6$ alkyl);

$R_{37}$ is $R_{36}$, phenyl optionally substituted by one or more $R_{36}$, phenoxy optionally substituted by one or more $R_{36}$, or benzyl optionally substituted by one or more $R_{36}$;

$R_{38}$ is a heterocyclic radical derived from a single heterocyclic ring or from a two ring fused heterocyclic system at least one ring of which is heterocyclic, each ring having 3 to 7 ring atoms, each heterocyclic ring having 1 to 4 hetero ring atoms selected from the group consisting of O, S and N, each ring being saturated or unsaturated and optionally having one or more substituents selected from the group consisting of $R_{36}$ and phenyl optionally substituted by one or more $R_{36}$;

$R_8$ and $R_9$, which are the same or different, are each H or $C_1$–$C_6$ alkyl optionally having one or more substituents selected from the group consisting of halogen, $NO_2$, CN, CHO, OH, $C_1$–$C_6$ alkoxy, $C_1$–$C_6$ alkylthio, $C_1$–$C_6$ alkylsulfinyl, $C_1$–$C_6$ alkylsulfonyl, ($C_1$–$C_6$ alkoxy) carbonyl, hydroxycarbonyl and carbamoyl;

$R_4$ is $R_{11}$ or $S(O)_n R_{11}$;

$R_{11}$ is $C_1$–$C_6$ alkyl, $C_3$–$C_6$ cycloalkyl or $C_4$–$C_8$ (cycloalkyl)alkyl, each of which is optionally substituted by one or more halogen;

n is 0, 1 or 2;

$R_5$ is H, halogen, CN, $S(O)_n R_8$, $OR_8$, $NR_8R_9$, $N(R_8)CON(R_9)(R_8)$, azido or —N=$C(R_{10})(OR_9)$;

$R_{10}$ has one of the meanings defined by $R_8$ above, or $R_{10}$ is benzyl or phenyl, each of which is optionally substituted by one or more $R_{36}$;

Z is N or C—$R_{16}$; and $R_{12}$, $R_{13}$, $R_{14}$, $R_{15}$ and $R_{16}$, which are the same or different, are each halogen, $R_8$, $OR_8$, $SF_5$, $S(O)_n R_8$, CN, $NO_2$, CHO, $C(O)R_8$ or $COOR_8$.

2. A compound according to claim 1, having one or more features selected from the group consisting of:

(a) Z is C—$R_{16}$;

(b) $R_{12}$ is chlorine or bromine;

(c) $R_{13}$ and $R_{15}$ are H;

(d) $R_{14}$ is perhaloalkyl, perhaloalkoxy or $SF_5$;

(e) $R_{16}$ is chlorine or bromine;

(f) $R_{31}$ is amino; alkyl optionally substituted by one or more $R_{35}$; phenyl optionally substituted by $R_{36}$ or $R_{37}$; $R_{38}$; NH—CO—NH—N=$CR_8R_9$; NH—CS—NH—N=$CR_8R_9$; NH—CO—$NR_8R_9$; NH—CS—$NR_8R_9$; NH—CO—$OR_8$; or NH—CS—$OR_8$;

(g) $R_{32}$ is $C_1$ to $C_6$ alkyl;

(h) $R_{33}$ is a lone pair of electrons or oxygen;

(i) $R_4$ is $S(O)_nR_{11}$;

(j) $R_{11}$ is methyl or ethyl;

(k) n is 0 or 1; and (l) $R_5$ is $NR_8R_9$.

3. A compound according to claim 1, wherein $R_{32}$ is $C_1$–$C_6$ alkyl.

4. A compound according to claim 1, wherein Z is C—$R_{16}$.

5. A compound according to claim 1, wherein $R_4$ is $S(O)_nR_{11}$.

6. A compound according to claim 1, wherein $R_{13}$ and $R_{15}$ are each H.

7. A compound according to claim 1, wherein $R_{14}$ is perhaloalkyl, perhaloalkoxy or $SF_5$.

8. A compound according to claim 3, wherein Z is C—$R_{16}$, $R_4$ is $S(O)_nR_{11}$, $R_{13}$ and $R_{15}$ are each H and $R_{14}$ is perhaloalkyl, perhaloalkoxy or $SF_5$.

9. A compound according to claim 3, wherein $R_{32}$ is $CH_3$.

10. A compound according to claim 5, wherein $R_{11}$ is $CH_3$ or $C_2H_5$.

11. A compound according to claim 9, wherein $R_4$ is $S(O)_nR_{11}$ wherein $R_{11}$ is $CH_3$ or $C_2H_5$.

12. A compound according to claim 7, wherein $R_{14}$ is $CF_3$, $OCF_3$ or $SF_5$.

13. A compound according to claim 1, wherein $R_{12}$ and $R_{16}$ are each Cl or Br.

14. A compound according to claim 12, wherein $R_{12}$ and $R_{16}$ are each Cl or Br.

15. A compound according to claim 1, wherein $R_5$ is $NR_8R_9$ wherein $R_8$ is H and $R_9$ is H or $C_1$–$C_6$ alkyl optionally substituted by CN, carbamoyl, ($C_1$–$C_6$ alkoxy) carbonyl, $C_1$–$C_6$ alkoxy, $C_1$–$C_6$ alkylthio, $C_1$–$C_6$ alkylsulfinyl or $C_1$–$C_6$ alkylsulfonyl.

16. A compound according to claim 1, wherein $R_{33}$ is a lone pair of electrons or oxygen.

17. A compound according to claim 1, wherein $R_{31}$, is $NH_2$; $C_1$–$C_{20}$ alkyl optionally substituted by one or more $R_{35}$; phenyl optionally substituted by one or more $R_{36}$ or $R_{37}$; $R_{38}$; NH—CO—NH—N=$CR_8R_9$; NH—CS—NH—N=$CR_8R_9$; NH—CO—$NR_8R_9$; NH—CS—$NR_8R_9$; NH—CO—$OR_8$; or NH—CS—$OR_8$.

18. A compound according to claim 1, wherein $R_{31}$ is $C_1$–$C_6$ alkyl optionally substituted by one or more $R_{35}$.

19. A compound according to claim 1, having the formula:

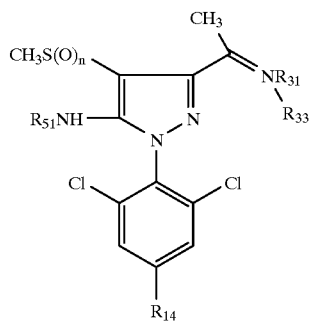

wherein:

$R_{33}$ is a lone pair of electrons or an oxygen atom;

n is 0, 1 or 2;

$R_{51}$ is H or $CH_3$;

$R_{14}$ is $CF_3$ or $SF_5$; and $R_{31}$ is H, $CH_3$ or cyclopropyl.

20. A compound according to claim 1, having the formula:

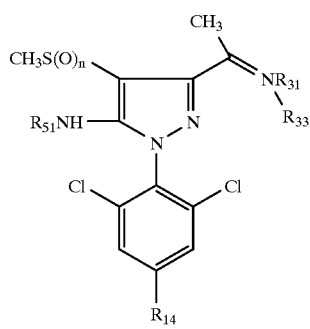

wherein:

$R_{33}$ is a lone pair of electrons or an oxygen atom;

n is 0, 1 or 2;

$R_{51}$ is H or $CH_3$;

$R_{14}$ is $CF_3$ or $SF_5$; and $R_{31}$ is $NH_2$, $NHC(O)OCH_3$, $NHC(O)NH_2$, $NHC(O)NHN=C(CH_3)_2$, $NHC(O)NHNH_2$ or $NHC(S)NH=C(CH_3)_2$.

21. A compound according to claim 1, having the formula:

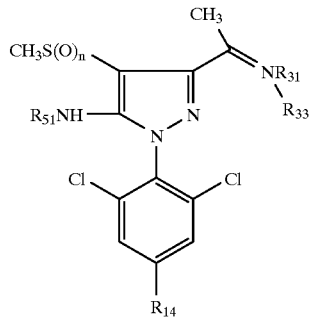

wherein:

$R_{33}$ is a lone pair of electrons or an oxygen atom;

n is 0, 1 or 2;

R$_{51}$ is H or CH$_3$;

R$_{14}$ is CF$_3$ or SF$_5$; and

R$_{31}$ is phenyl optionally having 1 to 3 substituents selected from the group consisting of methoxy, chloro, bromo, nitro, cyano, thiomethyl, fluoro, trifluoromethyl, methyl, sulfonylmethyl, NHC(O)CH$_3$ and hydroxy.

22. A compound according to claim 1, having the formula:

wherein:

R$_{33}$ is a lone pair of electrons or an oxygen atom;

n is 0, 1 or 2;

R$_{51}$ is H or CH$_3$;

R$_{14}$ is CF$_3$ or SF$_5$; and

R$_{31}$ is CH$_2$COOCH$_3$, CH$_2$CH$_2$OH, CH$_2$CH=CH$_2$ or CH$_2$(CN)$_2$.

23. A compound according to claim 1, having the formula:

wherein:

R$_{33}$ is a lone pair of electrons or an oxygen atom;

n is 0, 1 or 2;

R$_{51}$ is H or CH$_3$;

R$_{14}$ is CF$_3$ or SF$_5$; and

R$_{31}$ is a-methylbenzyl or benzyl optionally having one to three substituents selected from the group consisting of chloro, ethoxy, fluoro, methoxy, methyl and trifluoromethyl.

24. A compound according to claim 1, having the formula:

wherein:

R$_{33}$ is a lone pair of electrons or an oxygen atom;

n is 0, 1 or 2;

R$_{51}$ is H or CH$_3$;

R$_{14}$ is CF$_3$ or SF$_5$; and

R$_{31}$ is CH$_2$-(2-tetrahydrofuran) or CH$_2$-(2-furan).

25. A compound according to claim 1, having the formula:

wherein:

R$_{33}$ is a lone pair of electrons or an oxygen atom;

n is 0, 1 or 2;

R$_{51}$ is H or CH$_3$;

R$_{14}$ is CF$_3$ or SF$_5$; and

R$_{31}$ is a radical of the formula:

-continued

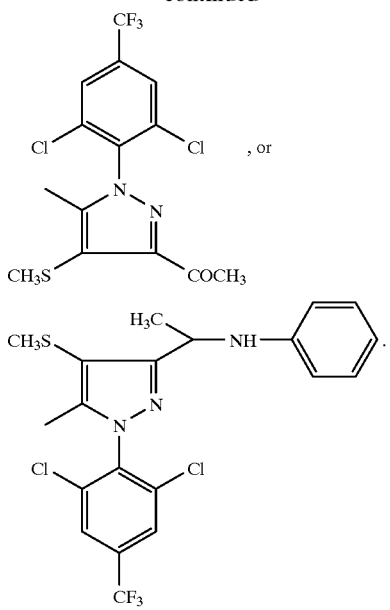, or

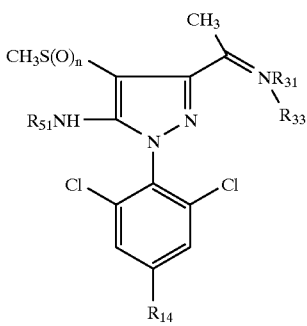

26. The compound according to claim 1, having the formula:

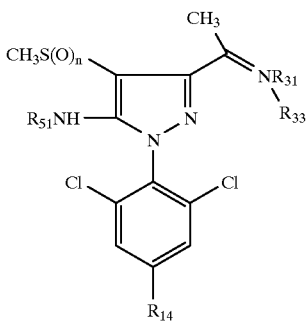

wherein $R_{33}$ is an oxygen atom, n is 1, $R_{51}$ is H, $R_{14}$ is $CF_3$ and $R_{31}$ is $CH_3$.

27. The compound according to claim 1, having the formula:

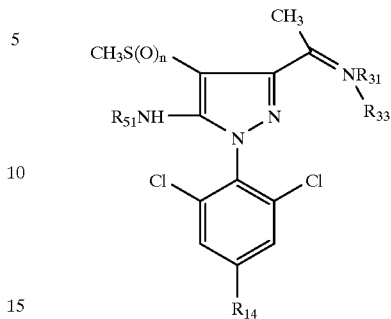

wherein $R_{33}$ is a lone pair of electrons, n is 1, $R_{51}$ is H, $R_{14}$ is $CF_3$ and $R_{31}$ is (4-methoxy)phenyl, (4-chloro)phenyl, (3,5-dimethoxy)phenyl, (3-cyano)phenyl, (3-hydroxy-4-methoxy)phenyl, (2-methyl)phenyl, (4-trifluoromethyl)phenyl, (3-trifluoromethyl-5-methoxy)phenyl, (3-fluoro-4-methoxy)phenyl, (3-chloro-4-bromo)phenyl or (3,5-dichloro-4-bromo)phenyl.

28. The compound according to claim 1, having the formula:

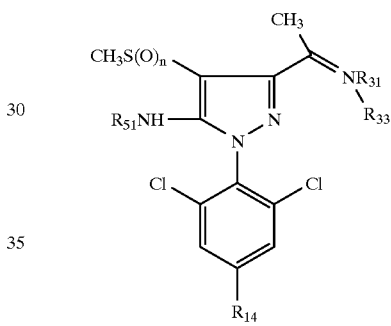

wherein $R_{33}$ is a lone pair of electrons, n is 1, $R_{51}$ is H, $R_{14}$ is $CF_3$ and $R_{31}$ is benzyl, (2-fluoro)benzyl, (4-fluoro)benzyl, (3-methoxy)benzyl, (α-methyl)benzyl, (2-methyl)benzyl, (3-methyl)benzyl, (4-trifluoromethyl)benzyl or (3-trifluoromethyl)benzyl.

29. The compound according to claim 1, having the formula:

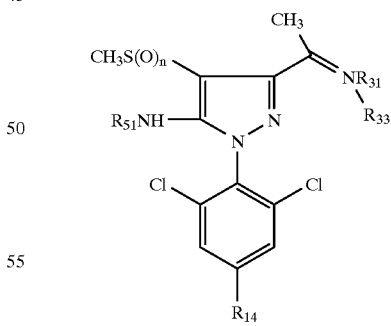

wherein $R_{33}$ is a lone pair of electrons, n is 1, $R_{51}$ is H, $R_{14}$ is $CF_3$ and $R_{31}$ is $CH_2$-(2-tetrahydrofuran) or $CH_2$-(2-furan).

30. The compound according to claim 1, having the formula:

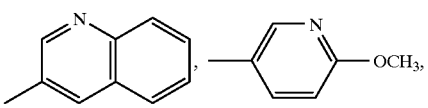

wherein $R_{33}$ is a lone pair of electrons, n is 1, $R_{51}$ is H, $R_{14}$ is $CF_3$ and $R_{31}$ is

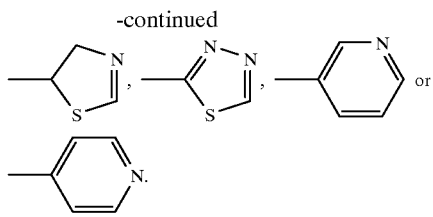

31. The compound according to claim 1, having the formula:

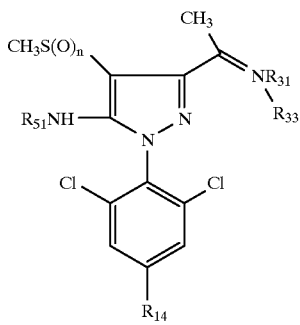

wherein $R_{33}$ is a lone pair of electrons, n is 1, $R_{51}$ is H, $R_{14}$ is $CF_3$ and $R_{31}$ is (3-methoxy-5-trifluoromethyl)phenyl, (3,5-dichloro)phenyl, (4-phenoxy)phenyl, (4-anilino)phenyl, (3-carbamoyl)phenyl, $-CH_2CH_2C(O)OCH_3$ or $CH_2C\equiv -CH$.

32. The compound according to claim 1, having the formula:

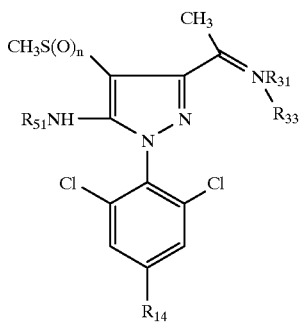

wherein $R_{33}$ is a lone pair of electrons, n is 1, $R_{51}$ is H, $R_{14}$ is $CF_3$ and $R_{31}$ is $(CH_2)_5CH_3$, $(CH_2)_4CH_3$, $(CH_2)_3CH_3$, $CH(CH_3)_2$, $CH_2CH_2CH_3$, $(CH_2)_6CH_3$, $(CH_2)_7CH_3$, $(CH_2)_8CH_3$, $(CH_2)_9CH_3$, $(CH_2)_8CH=CH(CH_2)_7CH_3$, $(CH_2)_{17}CH_3$, $(CH_2)_{11}CH_3$, $(CH_2)_{13}CH_3$, $(CH_2)_{10}CH_3$, $CH_2CH(CH_3)_2$, $CH_2CH_2CH(CH_3)_2$, $CH_2CH(CH_3)CH_2CH_3$, $CH(CH_3)CH(CH_3)_2$, $(CH_2)_{12}CH_3$ or $(CH_2)_{15}CH_3$.

33. A process for the preparation of a compound as claimed in claim 1, wherein $R_{33}$ is a lone electron pair, said process comprising reacting a compound having the formula:

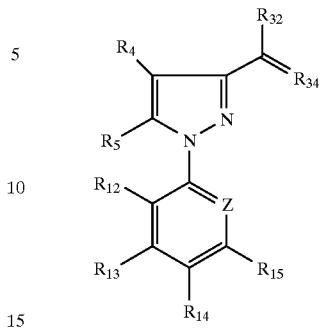

wherein $R_{34}$ is an oxygen atom and the remaining structural variables are as defined in claim 1, with an amine having the formula $$R_{31}-NH_2 \qquad (III)$$

wherein $R_{31}$ is as defined in claim 1.

34. A process for the preparation of a compound as claimed in claim 1 wherein $R_{33}$ is an oxygen or sulfur atom, said process comprising reacting a compound having the formula

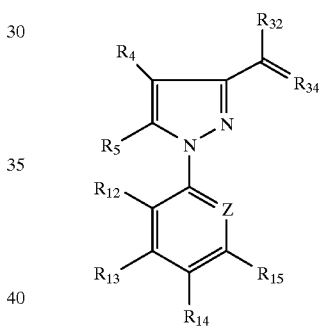

wherein $R_{34}$ is an oxygen atom and the remaining structural variables are as defined in claim 1, with an amine having the formula $$R_{31}-NHOH$$

or $$R_{31}-NHSH,$$

respectively, wherein $R_{31}$ is as defined in claim 1.

35. A method for controlling pests at a locus, said method comprising applying to said locus a pesticidally effective amount of a compound as claimed in claim 1, or a pesticidally acceptable salt thereof.

36. A method for controlling insects at a locus, said method comprising applying to said locus an insecticidally effective amount of a compound as claimed in claim 1, or an insecticidally acceptable salt thereof.

37. A method according to claim 36, wherein the insects are sucking insects.

38. A method according to claim 36, wherein the locus is an area used or to be used for the growing of crops.

39. A method according to claim 38, wherein the compound of formula (I) is applied at a rate of from about 5 g to about 1 kg/ha.

40. A method according to claim 36, wherein the locus is an animal.

41. A method according to claim 40, wherein the compound of formula (I) is applied at a rate of from about 0.1 to about 20 mg per kg body weight of animal per day.

42. A pesticidal composition comprising a pesticidally effective amount of a compound of formula (I) as claimed in claim 1, or a pesticidally acceptable salt thereof, and a pesticidally acceptable diluent or carrier therefor.

43. A pesticidal composition according to claim 42, comprising from about 0.05% to about 95% by weight of a compound of formula (I).

44. An insecticidal composition comprising an insecticidally effective amount of a compound of formula (I) as claimed in claim 1, or an insecticidally acceptable salt thereof, and an insecticidally acceptable diluent or carrier therefor.

* * * * *

UNITED STATES PATENT AND TRADEMARK OFFICE
CERTIFICATE OF CORRECTION

PATENT NO.:    5,965,491
DATED:         October 12, 1999
INVENTOR(S):   Tai-Teh WU et al.

It is certified that an error appears in the above-identified patent and that said Letters Patent is hereby corrected as shown below:

<u>IN THE CLAIMS</u>:

Claim 23, col. 41, line 64, "a-methylbenzyl" should read --$\alpha$-methylbenzyl--

Claim 31, col. 45, line 34, "$CH_2C\equiv$---CH" should read --$CH_2C\equiv CH$--

Signed and Sealed this

Eighteenth Day of April, 2000

Attest:

Q. TODD DICKINSON

*Attesting Officer*          *Director of Patents and Trademarks*